(12) United States Patent
Pedro Cossio et al.

(10) Patent No.: US 7,446,125 B2
(45) Date of Patent: Nov. 4, 2008

(54) DERIVATIVES OF NITROPROLINE COMPOUNDS, PROCESSES OF MANUFACTURE AND USES IN THE TREATMENT OF INTEGRIN MEDIATED DISORDERS

(75) Inventors: Fernando Pedro Cossio, Leioa (ES); Eneko Aldaba Arévalo, Leioa (ES); Yosu Ion Vara Salazr, Leioa (ES); Aizpea Zubia Olascoaga, Leioa (ES); Silvia Vivanco Amato, Leioa (ES); Miren Lorea Mendoza Arteche, Derio (ES); María Valcárcel Cuesta, Derio (ES); Fernando Vidal Vanaclocha, Derio (ES)

(73) Assignees: Universidad del Pais Vasco, Leioa (ES); Dominion Pharmakine S.L., Derio (ES)

(*) Notice: Subject to any disclaimer, the term of this patent is extended or adjusted under 35 U.S.C. 154(b) by 0 days.

(21) Appl. No.: 11/403,881

(22) Filed: Apr. 14, 2006

(65) Prior Publication Data

US 2006/0211630 A1    Sep. 21, 2006

Related U.S. Application Data

(60) Provisional application No. 60/672,201, filed on Apr. 15, 2005.

(51) Int. Cl.
*A61K 31/401* (2006.01)
*C07D 207/08* (2006.01)

(52) U.S. Cl. .................. 514/423; 514/426; 514/428; 548/537; 548/567; 548/570

(58) Field of Classification Search ............ 548/537, 548/567, 570; 514/423, 426, 428
See application file for complete search history.

(56) References Cited

OTHER PUBLICATIONS

Zubia et al, published online Apr. 13, 2005, Agnew. Chem. Int. Ed., 44(19), p. 2903-2907.*
Wikipedia encyclopedia, VLA-4.*
Wikipedia encyclopedia, Cancer.*
Annunziata et al., "1,3-Dipolar Cycloaddition Reactions of Azomethine Ylides on Enantiomerically Pure(E)-γ-Alkoxy-α,β-Unsaturated Esters," Tetrahedron Asymmetry, vol. 2 Issue 12, 1991, 1329-1342.
Galley et al., "Polyfunctionalized Pyrrolidines by Stereoselective 1,3-Dipolar Cycloaddition of Azomethine Ylides to Chiral Enones" 1995 American Chemical Society, J. Org. Chem. 1995, 60 p. 5005-5010.
Barr et al., "X=Y-ZH Compounds as Potential 1,3-Dipoles. Part 43[1] Metal Ion Catalysed Asymmetric 1,3-Dipolar Cycloaddition Reactions of Imines and Menthyl Acrylate," Tetrahedron vol. 51, No. 1, pp. 273-294, 1995.
Waldmann et al., "Asymmetric Control of 1,3-Dipolar Cycloaddition Reactions with Azomethine Ylides by Means of Proline Esters as Chiral Auxiliary Groups," Chem. Eur. J. 1995, 1:150-154.
Ayerbe et al., "Stereocontrolled Synthesis of Highly Substituted Proline Esters via [3+2] Cycloaddition between N-Metalated Azomethine Ylides and Nitroalkenes. Origins of the Metal Effect on the Stereochemical Outcome," J. Org. Chem. 1998, 63, 1795-1805.
Qian et al., "Expression of the Integrin α4β1 on Melanoma Cells Can Inhibit the Invasive Stage of Metastasis Formation," Cell Press, May 6, 1994, 77:335-347.
Matsuura, et al., "Induction of Experimental Bone Metastasis in Mice by Transfection of Integrin α4β1 into Tumor Cells," American Journal of Pathology, Jan. 1996, 148:55-61.
Okada et al., "Significance of VLA-4-VCAM-1 interaction and CD44 for transendothelial invasion in a bone marrow metastatic myeloma model," Clin. Exp. Metastasis 1999; 17:623-629.
Papadimitriou et al., "Integrin $α_4β_1$/VCAM-1 pathway mediates primary adhesion of RAW117 lymphoma cells to hepatic sinusoidal endothelial cells under flow," Clin. Exp. Metastasis 1999; 17:669-676.
Vidal-Vanaclocha et al., Interleukin-1 Receptor Blockade Reduces the Number and Size of Murine B16 Melanoma Hepatic Metastases[1], Cancer Research 54, 2667-2672, May 15, 1994.
Anasagasti et al., "Sinusoidal Endothelium Release of Hydrogen Peroxide Enhances Very Late Antigen-4-Mediated Melanoma Cell Adherence and Tumor Cytotoxicity During Interleukin-1 Promotion of Hepatic Melanoma Metastasis in Mice," Hepatology, Apr. 1997, 25:840-846.
Mendoza et al., "Hydrogen Peroxide Mediates Vascular Cell Adhesion Molecule-1 Expression From Interleukin-18-Activated Hepatic Sinusoidal Endothelium: Implications for Circulating Cancer Cell Arrest in the Murine Liver," Hepatology, Aug. 2001, 34:298-310.
Vidal-Vanaclocha et al., "IL-18 regulates IL-1β-dependent hepatic melanoma metastasis via vascular cell adhesion molecule-1," PNAS, Jan. 18, 2000, 97:734-739.
Wattanasin et al., "Design and Synthesis of Potent and Selective Inhibitors of Integrin VLA-4," Bioorganic & Medicinal Chemistry Letters 11 (2001) 2955-2958.
Kopka et al., "Substituted N-(3,5-Dichlorobenzenesulfonyl)-L-prolyl-phenylalanine Analogues as Potent VLA-4 Antagonists," Bioorganic & Medicinal Chemistry Letters 12 (2002) 637-640.
Chen et al., "N-Acyl-$_L$-phenylalanine Derivatives as Potent VLA-4 Antagonists that Mimic a Cyclic Peptide Conformation," Bioorganic & Medicinal Chemistry Letters 12 (2002) 137-140.
Lin et al., "Specific and Dual Antagonists of $α_4β_1$ and $α_4β_7$ Integrins," Bioorganic & Medicinal Chemistry Letters 12 (2202) 133-136.
de Groot et al., "Design, Synthesis, and Biological Evaluation of a Dual Tumor-specific Motive Containing Integrin-targeted Plasmin-cleavable Doxorubicin Prodrug[1]," Molecular Cancer Therapeutics; Sep. 2002, 1:901-911.
Azuma et al., "Marked Prevention of Tumor Growth and Metastasis by a Novel Immunosuppressive Agent, FTY720, in Mouse Breast Cancer Models," Cancer Res., Mar. 1, 2002, 62:1410-1418.

* cited by examiner

*Primary Examiner*—Joseph McKane
*Assistant Examiner*—Yong Chu
(74) *Attorney, Agent, or Firm*—Darby & Darby

(57) ABSTRACT

This invention relates to nitroproline derivative compounds and procedures for their preparation and the preparation of pharmaceutical compositions containing the compounds. The invention also relates to the administration of compounds of the invention as agents for the treatment of mammalian diseases whose pathogenic and pathophysiological mechanisms depend on or are significantly contributed by undesirable cellular and molecular activities or responses induced by integrin-dependent molecular interactions.

9 Claims, 10 Drawing Sheets ically-related agents (Azuma et al. Cancer Res. 2002, 62,1410).
DERIVATIVES OF NITROPROLINE COMPOUNDS, PROCESSES OF MANUFACTURE AND USES IN THE TREATMENT OF INTEGRIN MEDIATED DISORDERS This application claims the benefit of priority of U.S. Provisional Patent Application No. 60/672,201, filed Apr. 15, 2005, which is hereby incorporated by reference. Spanish Patent Application No. 200300837, filed Apr. 9, 2003, is hereby incorporated by reference.

In one embodiment, the invention is related to new nitroproline derivative compounds, with procedures for their preparation and with the use thereof as agents for the treatment of mammalian diseases whose pathogenic and pathophysiological mechanisms depend on or are significantly contributed by undesirable cellular and molecular activities or responses induced by integrin-dependent molecular interactions.

Pyrrolidine rings can be synthesized by means of 1.3-dipolar reactions between azomethine ylides and unsaturated compounds, such as alkenes and alkynes (Kanemasa and Tsuge, in Advances in Cycloaddition Chemistry; Curran, D. P., Ed. Jai Press: Greenwich, Conn., 1993; Vol.3, p. 99-159).

Also known is the reaction between azomethine ylides and homochiral alfa, beta-unsaturated carbonylic compounds for the stereocontrolled preparation of highly-substituents chiral pyrrolidines (Annunciatta et al., Tetrahedron: Asymmetry 1991, 2, 1329. Galley et al. J. Org. Chem. 1995, 60, 5005. Barr et al. Tetrahedron 1995, 51, 273. Waldmann et al. Chem. Eur. J. 1995, 1, 150). Also known is the reaction between metalated azomethine ylides with homochiral nitroalkene derivatives of methyl L-lactate and of isopropylidene glyceraldehyde, giving rise to homochiral pyrrolidine rings with moderate stereocontrol (Ayerbe et al. J. Org. Chem. 1998, 63, 1795).

On the other hand, the integrin-ligand complexation processes are known to be involved in cell-cell interaction mechanisms contributing to the processes of embryogenesis, neurogenesis, regeneration, immune response, inflammation, hematopoiesis, angiogenesis, and cancer metastasis. In this particular case, the binding of integrin VLA-4 (very late antigen-1) with the VCAM-1 (vascular cell adhesion molecule-1) ligand is involved in the metastasis process of melanoma (Quian et al. Cell 1994, 77, 335), renal cancer (Tomita et al. Int. J. Cancer 1995, 60, 753), bone cancer (Matsumura et al. Am. J. Pathol. 1996, 148, 55), stomach cancer (Yasoshima et al., Jpn. Cancer Res. 1996, 87, 153), myeloma (Okada et al. Clin Exp Metastasis. 1999;17:623-9) and lymphoma (Papadimitron et al., Clin. Exp. Metastasis 1999, 17, 669). The formation of metastasis by circulating tumor cells requires a prior process of tumor cell adhesion to the vascular system endothelial wall that is controlled by adhesion molecules activated by proinflammatory factors (cytokines) (Weiss et al. Clin Exp Metastasis 1989;7:127). Using murine B16 melanoma, it has been demonstrated that the implantation of tumor cells in the microvascular system of the liver (hepatic sinusoids) precedes the formation of metastasis (Vidal-Vanaclocha et al. Int J Cancer. 1990;46:267-71). The process is controlled by soluble factors released by tumor cells(Vidal-Vanaclocha et al. Cancer Res. 1994;54:2667-72). Factors such as these activate the expression of the VCAM-1 adhesion molecule on the surface of the hepatic sinusoid endothelium, which, in turn, allows the endothelial adhesion of the melanoma cells which express the VLA-4 integrin (VCAM-1 ligand) (Anasagasti et al. Hepatology. 1997;25:840-6. This stage conditions other later stages in the metastasis process because antibodies directed against endothelial VCAM-1 or tumoral VLA-4 integrin prevent the formation of metastasis (Mendoza et al. Hepatology 2001;34:298-310). However, VCAM-1 appears at the end of a proinflammatory cytokine cascade generated by the activated endothelium, in which TNF-α, IL-1β and IL-18 are consecutively involved (Vidal-Vanaclocha et al. Proc. Natl. Acad. Sci. USA 2000, 97, 734). The last-mentioned of these cytokines induces the endothelial expression of VCAM-1 by means of an $H_2O_2$-dependent mechanism (Mendoza et al. Hepatology 2001 ;34:298).

Although different researchers have prepared non-natural inhibitors of the in-vitro interaction between VLA-4 and VCAM-1 (Boer et al., Angew. Chem. Int. Ed. 2001, 40, 3870; Wattanassin et al., Bioorg. Med. Chem. Lett. 2001, 11, 2955; Kopla et al., Bioorg. Med. Chem. Lett. 2002, 12, 637; Chen et al. Bioorg. Med. Chem. Lett. 2002, 12, 137; Lin et al., Bioorg. Med. Chem. Lett. 2002, 12, 133), these compounds have only been tested in in-vitro adhesion models not related to cancerous metastasis, their effectiveness in this field thus not having been proven.

Apart from this, these compounds may present bioavailability issues, either because their in vivo absorption is not adequate or is unknown, or because their peptidic nature based on natural cyclic amino acids, makes them readily degradable by proteolytic enzymes. Thus, for example, it has been published that some bicyclic peptides including RGD sequences inhibit the adhesion of tumor cells by means of their interaction with $α_vβ_3$ and $α_vβ_5$, but not $α_4β_1$ type integrins. However, these peptides, under highly stable physiological conditions, have not been tested in experiments with complete organisms (de Groot et al. Mol. Cancer Therapeutics 2002, 1, 901). Likewise, the experimental inhibition of cancer metastasis has recently been published in lung, liver and kidneys of mice by the immunossuppressing agent BTY720 (a 2-amino-1,3-acyclic propanodiol), presumably by means of a different process such as is the reduction of integrin expression, although the hypothetical nature of the mechanism of antimetastaic action hinders the development of other. structurally-related agents (Azuma et al. Cancer Res. 2002, 62,1410).

SUMMARY OF THE INVENTION

Nitroproline derivatives are inhibitors of the binding between VLA-4 and VCAM-1, which additionally entail advantages such as their good pharmacodynamic properties, their chemical stability in solid phase and in solution, the ease and efficiency of the chemical synthesis and, lastly, the accessibility and variability of the starting reagents.

These unnatural synthetic small molecules designed to mimic the minimal requirements for binding between the natural macromolecules completely abrogate melanoma cell adhesion to cytokine-activated endothelial cells, melanoma cell responses to soluble and immobilized VCAM-1 and efficiently inhibit metastatic development in vivo, without significantly affecting their cell viability, proliferation rate and major metabolic activities. Second, they also prevent both Jurkat leukemia cell and human peripheral blood-derived lymphocyte cell adhesion to immobilized VCAM-1 substrate. Third they inhibit leucocyte recruitment into unaffected tissue of liver bearing colon carcinoma metastases. Fourth, they inhibit endothelial cell and myofibroblast recruitment into colon carcinoma hepatic metastases in vivo and endothelial cell migration induced by tumor-derived soluble factors in vitro, all which correlates with decreased angiogenesis and low metastatic growth in vivo.

The present invention discloses a novel group of compounds that are derivatives of nitroprolines showing the following formula (I):

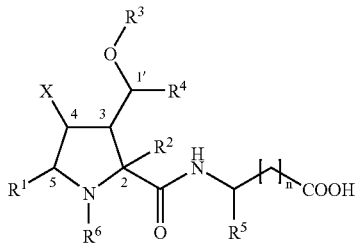

wherein:
or any of the salts thereof, wherein:

n is selected from 0 to 5;

$R^1$, $R^3$ and $R^4$ all individually represent a group selected from a substituted or unsubstituted C1-C8 alkyl. (cyclic, linear or branched), substituted or unsubstituted phenyl, benzyl, aryl or heteroaryl;

wherein the substituents groups may be substituted with 1-6 atoms or groups selected from halogen, linear, branched or cyclic alkyl or alkoxy, Benzyloxy, trifluoromethyl, trichloromethyl, nitro, hydroxyl or amino groups;

$R^2$ represents a hydrogen atom or a C1-C8 linear or branched alkyl group;

$R^5$ and $R^6$ represents a hydrogen or a group selected from a straight, branched or cyclic alkyl, aryl, heteroaryl, mono- or polysubstituents aryl, mono- or polysubstituents heteroaryl, benzyl or mono- or polysubstituents benzyl; and (X) represents a group selected from nitro, amido or amino.

In one preferred embodiment of the present invention provides a compound of formula 1, which are derivatives of chiral nitroprolines with (R) or (S)-configuration carbons C2, C3, C4, C5 and C3-1', as a way of example, but not limited to, the compounds of the following formula:

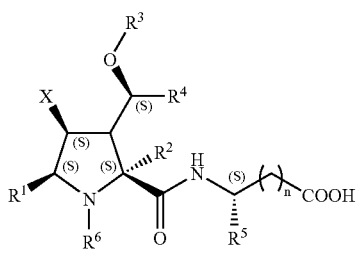

In other preferred embodiment of the present invention provides a compound of formula (I) wherein (X) is a nitro and $R^5$ and $R^6$ is a hydrogen atom.

In another preferred embodiment of the present invention provides a compound of formula (I) wherein (X) is a nitro, $R^5$ and $R^6$ is a hydrogen atom and $R^1$ is a substituted or unsubstituted C1-C8 alkyl (cyclic, linear or branched) or a phenyl group.

In another preferred embodiment of the present invention provides a compound of formula (I) wherein (X) is a nitro, $R^5$ and $R^6$ is a hydrogen atom, and $R^2$ is a hydrogen atom or a methyl group.

In another preferred embodiment of the present invention provides a compound of formula (I) wherein (X) is a nitro, $R^5$ and $R^6$ is a hydrogen atom and $R^3$ is a substituted or unsubstituted benzyl.

In another preferred embodiment of the present invention provides a compound of formula (I) wherein (X) is a nitro, $R^5$ and $R^6$ is a hydrogen atom and $R^4$ is a linear or branched C1-C8 alkyl.

In another preferred embodiment of the present invention provides a compound of formula (I) wherein (X) is a nitro, $R^5$ and $R^6$ is a hydrogen atom, $R^1$ is phenyl, cyclohexyl, cyclopropyl, substituted or unsubstituted butyl, $R^2$ is an hydrogen atom or a methyl group, $R^3$ is a substituted or unsubstitutes benzyl, wherein the substitutients are one or two fluorine atoms, and $R^4$ is an isopropyl or sec-butyl.

Compounds of the present invention have been designed, synthesized and developed based on the geometric and electronic features of the VLA-4NCAM-1 interaction moieties in the natural binary system. Structural and electronic features of VCAM-1 have been first examined in order to reproduce these features in the synthetic inhibitors. The crystal structure of domains 1 and 2 of VCAM-1 has been resolved by X-Ray diffraction analysis. In addition, directed mutagenesis studies have determined that the CD loop in domain 1 of VCAM-1 is crucial for binding to VLA-4 (FIG. 1A). In the solvated molecule, the carboxymethyl group of Asp4O has a considerable conformational freedom and is surrounded by a relatively hydrophobic environment (FIG. 1 B). We reasoned that compounds above-mentioned could mimic the structural and electronic features of the Ile39-Asp40-Ser41-Pro42 sequence of domain 1 of VCAM-1 (FIG. 1C).

Thus, the carboxymethylamido chain of these novel compounds reproduces the binding ability of Asp40, whereas the remaining groups provides the environment required for simulating the structural and electrostatic features of the remaining residues. In addition, the pyrrolidine ring confers to the molecule the restriction of conformational freedom necessary to mimic the energetically available conformations of the CD loop in the β-barrel of domain 1 of VCAM-1 (FIGS. 1B, C). Therefore, these unnatural highly substituents pyrrolidine rings should bind to VLA-4, thus disrupting VLA-4NCAM-1 interaction-dependent mechanisms.

A second aspect of this invention is the preparation of said compounds of general formula (I).

The process for the preparation of formula (I) nitroproline derivative compounds includes making a mixture comprised of the following react in an organic solvent:

a) a chiral nitroproline derivative compound with (R) or (S)-configuration carbons C2, C3, C4, C5 and C3-1', of the following formula (II),

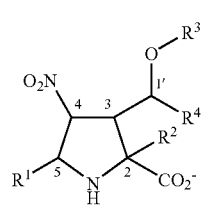

wherein:
$R^1$, $R^2$, $R^3$ and $R^4$ represent that which has been previously stated hereinabove;

b) a salt of an alfa- or beta-aminoester with the following formula (III),

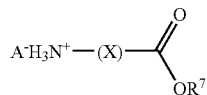
(III)

wherein:
(X) represents that which has been previously stated hereinabove;
A⁻ represents a group selected from a chloride, bromide, iodide, mesilate or tosilate anion; and
R⁷ represents a C1-C6 alkyl or aryl group;
  c) a carboxyl group activation reagent, and
  d) a tertiary organic base, selected from the aliphatic bases with C3-C10 carbons or alkane aromatic bases with C9-C15 carbons.

For the purposes of the invention, the reaction mixture comprised of the four components stated hereinabove can be made by adding one of the compounds to the mixture prior to the other three in the organic solvent at the temperature of −85° C. to +25° C., preferably at temperatures nearing zero degrees centigrade. Afterward, it is left for a length of time to complete the reaction, being able to reach ambient temperature. Once the ester resulting from the prior coupling reaction has been separated, said product is reacted with a mixture of lithium hydroxide, dimethoxyethane and water, thus yielding, following the corresponding treatment, the compounds of formula I specified hereinabove.

The preparation of the formula (II) compound mentioned hereinabove is made in an organic solvent, such as acetonitryle or ethyl ether, by reacting a mixture comprised of the following:
  a) an (R) or (S) chiral nitroalkene with the following formula (IV),

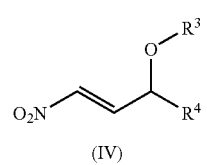
(IV)

wherein R³ and R⁴ represent that previously stated hereinabove;
  b) a generally chiral imine of (R) or (S) configuration with the following formula (V),

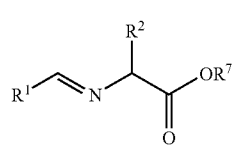
(V)

wherein R² and R¹ represent that which has been previously stated hereinabove and R⁷ represents a C1-C6 alkyl or aryl group;
  c) a metallic salt, preferably selected from silver acetate, silver perchlorate and lithium perchlorate, and
  d) a tertiary organic base, selected from the aliphatic bases with C3-C10 carbons or alkane aromatic bases with C9-C15 carbons.

For the purposes of the invention, the reaction mixture comprised of the four components stated hereinabove can be made by adding one of the compounds to the mixture prior to the other three in the organic solvent at the temperature of −25° C. to +25° C., preferably at temperatures nearing zero degrees centigrade. Afterward, it is left for a length of time to complete the reaction, being able to reach ambient temperature.

Once the ester resulting form the prior cycloaddition reaction has been separated, said product is reacted with a mixture of lithium hydroxide, dimethoxyethane and water, thus yielding, following the corresponding treatment, the compounds of the specified formula (II).

A third aspect of the present invention provides a method of treatment of cancer metastasis using the compounds of the formula (I), preferably for the metastasis of melanoma.

The mechanism of action of said compounds is explained by their antagonist properties with the VLA-4 integrin expressed by the tumor cells. These properties hinder or block the VLA-4/VCAM-1 binding, which means an inhibition of tumor cell adhesion to the vascular walls followed by an inhibition of metastasis.

A fourth aspect of the present invention provides a method of inhibiting binding of a VLA-4 to a protein ligand comprising contacting VCAM-1 with a compound of the formula (I).

Another additional aspect of the invention is the use of these derivatives of general formula (I) for the treatment of cancer metastasis, preferably for the metastasis of melanoma.

Lastly, the aspect of this invention involves the preparation of a composition that includes at least one of the compounds of general formula (I) and one or more pharmaceutically-acceptable excipients. The compounds in formula (I) of his invention can be administered both as pure substance as well as in the pharmaceutical formulation form, although it is preferable for the compound to be administered in combined form. The combination of the drug is preferably in the form of a formulation which (1) contains only the compound in general formula I (2) contains one or more excipients and/or carrier substances and (3) may contain some additional therapeutically-active substance.

The excipients, carrier substances and auxiliary substances must be pharmaceutically and pharmacologically tolerable, so that they may be combined with other components in the formulation or preparation and will not have any adverse effects on the organism treated.

The formulations includes those which are suitable for oral or parenteral administration (including subcutaneous, intradermal, intramuscular and intravenous), although the best way of administering the formulations depends on the condition of the patient in question.

The formulations can be in single-dose form. The formulations are prepared in accordance with known methods in the pharmacology field. The quantities of active substances for administering may vary in terms of the individual aspects of the therapy in question.

For a reader comprehension of the preceding ideas, a description is provided hereinbelow of some examples of the embodiment of this invention merely for purposes of illustration.

EXAMPLE 1

Figure 1:
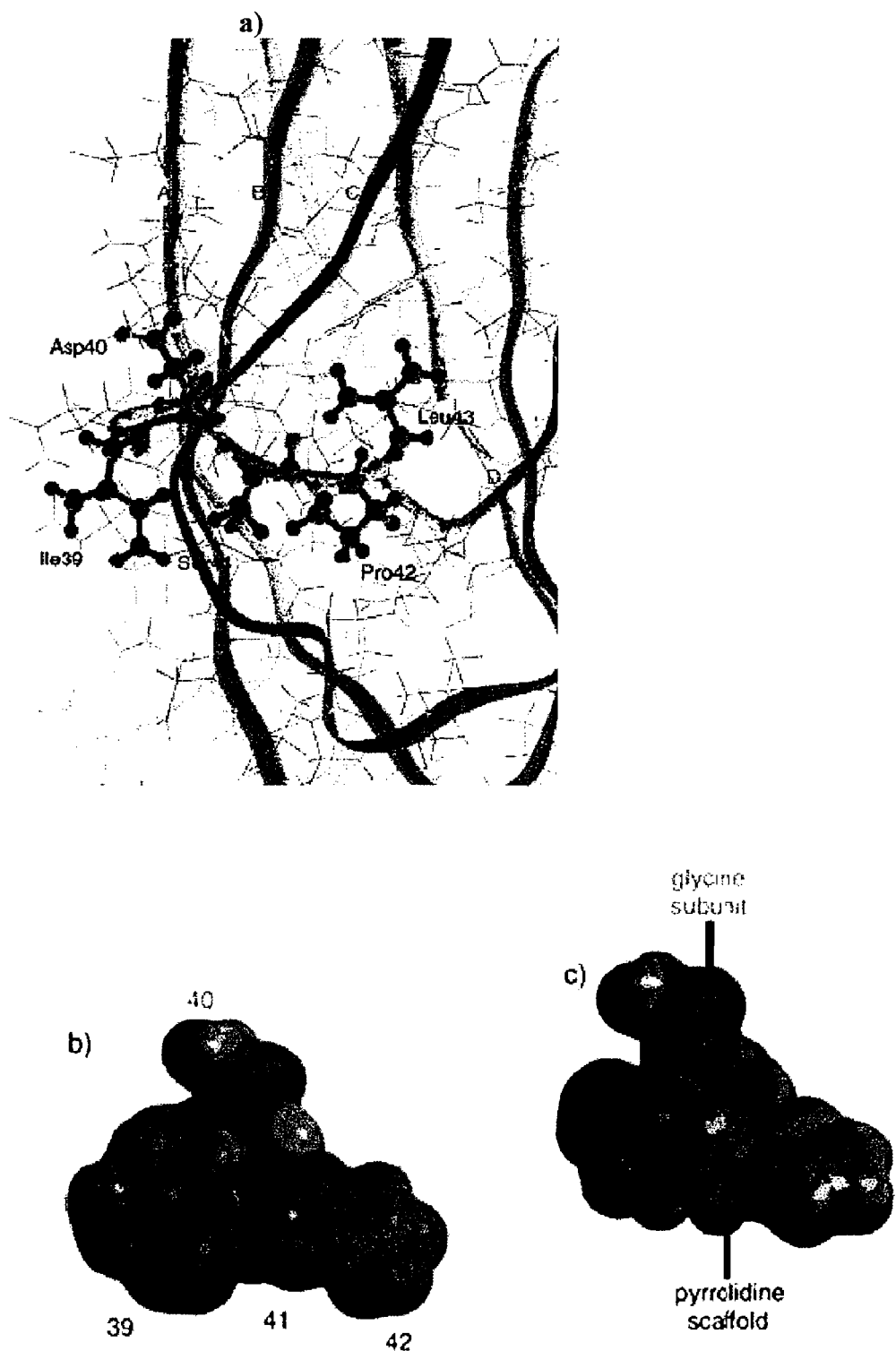
FIG. 1A shows the X-Ray structure of the active loop of VCAM-1 involved in binding with integrin VLA-4.
FIG. 1B Show electrostatic potential projected onto the electron density of the Ile$_{39}$-Asp$_{40}$-Ser$_{41}$-Pro$_{42}$ tetramet and, FIG. 1C, inhibitor 11d. Energies range from −138.2 kcal mol$^{-1}$ (red) to +100.2 kcal mol$^{-1}$. Asterisks (*) indicate the hydrophobic regions in both structures.

Synthetic Routes for the Preparation of Compounds of Formula

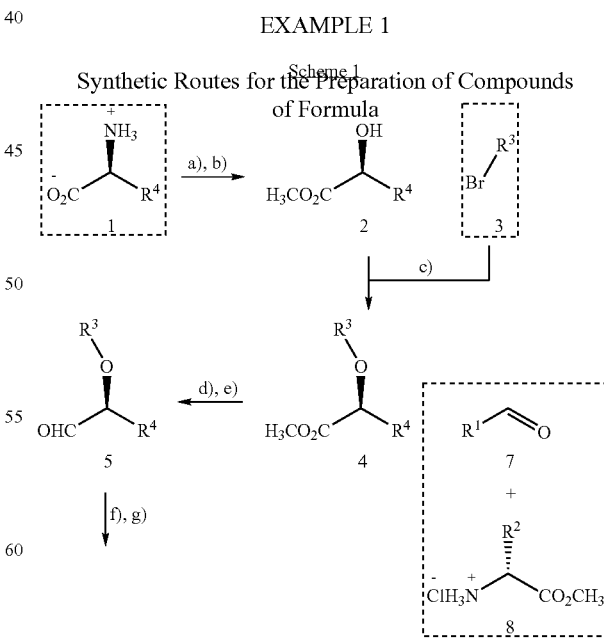

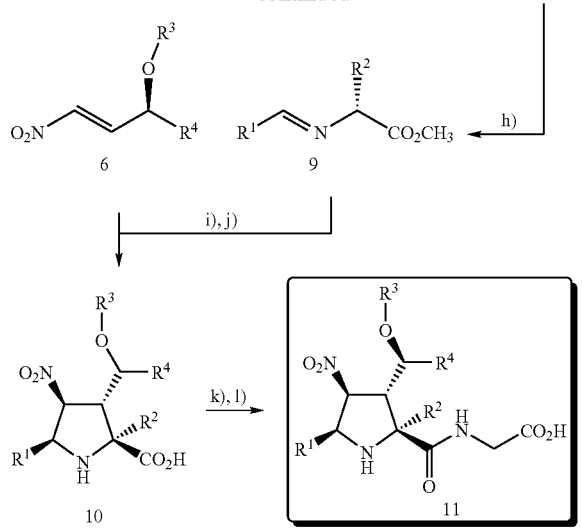

a Michael-type nucleophilic attack of the carbon atom of the azomethine ylide A, which forms in situ, on the b carbon atom of the nitroalkene (Scheme 1). The cyclization step takes place by means of an intramolecular Henry-type reaction between the intermediate nitronate moiety and the iminic fragment of the zwitterionic intermediate denoted as B in Scheme 1.

Scheme 1 shows the chemical synthesis of compounds 11 wherein TEA is triethylamine; MsCl is methanesulphonyl chloride; DIPEA is N,N-diisopropylethylamine. DMP is 2,2-dimethoxypropane; TsOH.H$_2$O is p-toluenesulfonic acid monohydrate; DMF is N,N-dimethylformamide; THF is tetrahydrofurane; DMSO is dimethyl sulphoxide; DME is 1,2-dimethoxyethane; DECP is diethyl cyanophosphonate; RT is room temperature. Numbers before reagents denote mole equivalents; % denotes yields of isolated products. (a) 1.0 1 in H$_2$SO$_4$ 1 N at 0° C., followed by 1.5 NaNO$_2$ in H$_2$O at 0° C. for 24 hours, 83-90%. (b) 1.0 DMP, 0.007 TsOH.H$_2$O in MeOH at 45° C. for 24 hours, 88-96%. (c) 1.0 2 in dry THF/DMF anhydrous 2:0.6, 0° C., followed by 1 NaH, 0° C., 10 min; then 1.2 3 at RT for 24 hours, 45-64%. (d) 1 LiAlH$_4$ in Et$_2$O at 0° C., followed by 1.0 4 in Et$_2$O at RT for 3 hours, 80-90%. (e) 1.5 ClCOCOCl, 2.0 DMSO, 4.0 TEA in CH$_2$Cl$_2$ at −67° C. for 5 hours, 79-90%. (f) 1 5, 5 CH$_3$NO$_2$, 0.14 TEA at RT, overnight, 87-96%. (g) 1.2 MsCl, 2.5 DIPEA in CH$_2$Cl$_2$ at −78° C. for 2 hours, 85-95%. (h) 1.15 8, 1.25 TEA, MgSO$_4$ in CH$_2$Cl$_2$ at RT for 1 hour, followed by 1.0 7 at RT, overnight, 75-95%. (i) 1.0 6, 1.0 9, 0.1 AgOAc, 1 TEA in CH$_3$CN at RT for 5 hours, 60-92%. (j) DME/LiOH aq 1N 5:3 at 0° C. for 1-4 hours, 82-95%. (k) 1.0, 1 glycine methyl ester hydrogen chloride, 1.2 DECP in DMF at 0° C., followed by 2.0 TEA at RT overnight, 64-95%. (l) in DME/LiOH aq 1 N 5:3 at 0° C. for 1-4 hours, 85-97%.

The new compounds 11 were synthesized in 12 preparative steps according to the design depicted in Table 1 and Scheme 1 (for more details, see Supporting Information). The starting materials were readily accessible and inexpensive chemicals such as /-a-amino acids (glycine, alanine, valine, and leucine), halides 3, and aldehydes 7. The key step in the synthetic route shown in Scheme 1 is the formal [3+2] cycloaddition between E-nitroalkenes 6 and imines 9 to yield pyrrolidines 10. This reaction takes place with complete stereocontrol when R1 is a phenyl group, and R4 is isopropyl or sec-butyl (compounds 10 a, c-e, g, i, j). When R1 is an alkyl group, the stereocontrol is variable and ranges from greater than 99:1 when R1=tBu (10b) to 91:9 when R1=cHex (10 f) or cPr (10h). In the case of pyrrolidine 10k, which has a chiral group at R1, three stereoisomers were obtained in a ratio of 77:15:8. Previous studies[6] have shown that the reaction between p-deficient alkenes and metalated azomethine ylides takes place through a stepwise mechanism, not a concerted mechanism, to give the [3+2] cycloadduct. The first step comprises

TABLE 1

Structure of compounds 11.

| Compound 11 | R$^1$ | R$^2$ | R$^3$ | R$^4$ |
|---|---|---|---|---|
| a | Phenyl | H | Benzyl | Isopropyl |
| b | t-butyl | H | Benzyl | Isopropyl |
| c | Phenyl | H | 2-F-benzyl | Isopropyl |
| d | Phenyl | H | Benzyl | Sec-butyl |
| e | Phenyl | H | 2,6-diF-benzyl | Isopropyl |
| f | Cyclohexyl | H | Benzyl | Sec-butyl |
| g | Phenyl | H | 3,5-diF-benzyl | Sec-butyl |
| h | Cyclopropyl | H | Benzyl | Sec-butyl |
| I | Phenyl | H | 2,3-diF-benzyl | Sec-butyl |
| J | Phenyl | Methyl | Benzyl | Sec-butyl |

TABLE 1-continued

Structure of compounds 11.

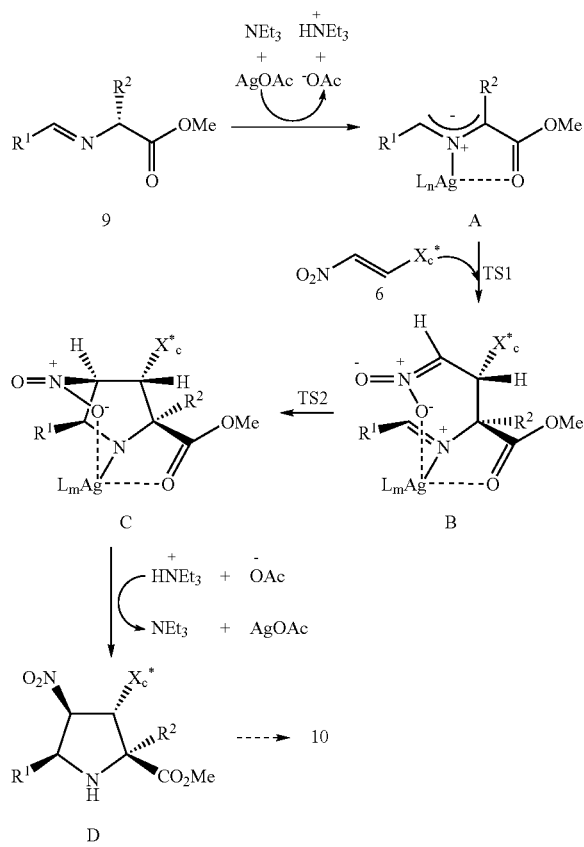

| Compound 11 | R¹ | R² | R³ | R⁴ |
|---|---|---|---|---|
| K | ![sec-butyl with OCH2Ph] | H | Benzyl | Sec-butyl |

Scheme 2.-Mechanism of formation of cycloadducts 10.

Scheme 2 shows the mechanism of formation of cycloadducts 10 from the reaction between imines 9 and nitroalkenes 6. Wherein $X_c$ is a chiral group.

Figure 2:
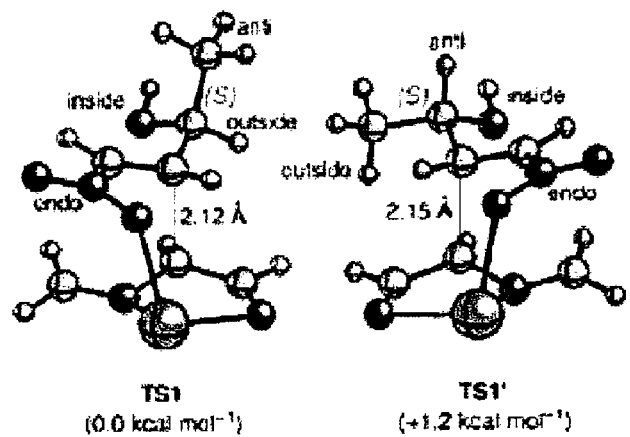
FIG. 2 Ball & Stick representation of the fully optimized structures of transition structures TS1 and TS1'. Elements are represented as follows: carbon, oxygen, nitrogen, silver.
Figure 5:
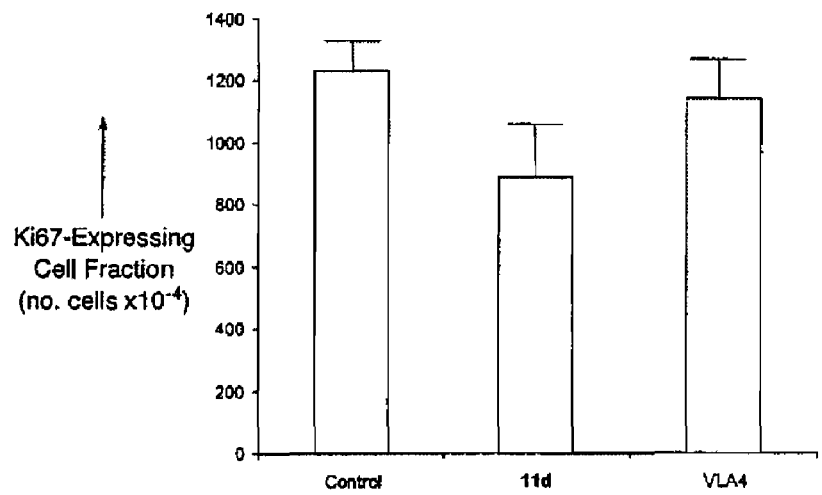
FIG. 5 shows the effect of compound 11d and anti-murine VLA-4 antibody on B16M cell proliferation in vitro.

To understand the origins of the stereocontrol of the reaction, we computed the two possible diastereomeric transition-state structures TS1 and TS1' for the model system depicted in FIG. 5. As shown in FIG. 5 and Scheme 1, part of the stereocontrol of the reaction stems from the retention of configuration of the E-nitroalkene and the chelated nature of the metalated azomethine ylide. The diastereoselectivity can be explained in terms of a two electron interaction between the localized s* orbital of the C_C bond that forms and the localized s orbital of the antiperiplanar C_CH3 bond, with the alkoxy group occupying the inside position with respect to the pyrrolidine ring that forms, as seen in FIG. 2.

EXAMPLE 2

General Procedure for the Synthesis of α-Benzyloxy Esters 4.

To a solution of L-amino acid 1 (25.0 mmol) in $H_2SO_4$ 2N (37.5 ml, aqueous solution), cooled to 0° C., was added a solution of $NaNO_2$ 2N (2.57 g, 37.0 mmol) in water (9 ml). The temperature was maintained below 5° C. during the addition, and the mixture was stirred at such a temperature for 24 h. The solution was saturated with $(NH_4)_2SO_4$, extracted with ether (3×25 ml), dried over $Na_2SO_4$ and evaporated under reduced pressure giving 2.72 g (23.0 mmol) of the corresponding α-hydroxy acid as an oil. A solution of this oily material, p-toluenesulfonic acid monohydrate (0.03 g, 0.16 mmol) and dimethoxypropane (2.8 ml, 23.0 mmol) in methanol (1.15 ml) was heated at 45° C. for 24 h. The reaction mixture was evaporated under reduced pressure providing the corresponding □hydroxy methyl ester 2 as an oil. This material was dissolved in anhydrous tetrahydrofuran (40 ml) and anhydrous N,N-dimethylformamide (12 ml), under an inert atmosphere, was cooled to 0° C. NaH (0.48 g, 20.0 mmol) was added and the mixture was stirred for 10 min. The corresponding bromide 3 (24.0 mmol) was added dropwise, and the mixture was allowed to reach room temperature. The reaction was monitored by TLC. When the reaction was complete, the reaction mixture was diluted in ether (130 ml) and washed with water (3×50 ml). The remaining organic layer was dried over $Na_2SO_4$ and evaporated under reduced pressure, providing the crude product 4, which was purified by flash column chromatography.

(S)-Methyl 2-(benzyloxy)-3-methylbutanoate. This compound was previously described by Jouillé et al. See: W.-R. Li, W. R. Ewing, B. D. Harris, M. M. Jouillé J. Am. Chem. Soc. 1990, 112, 7659.

(S)-Methyl 2-(2-fluorobenzyloxy)-3-methylbutanoate. This compound was prepared from L-valine and 2-fluorobenzyl bromide in 40% yield: bp 70-72° C. (0.5 mm Hg); IR 1751, 1229 cm$^{-1}$; $^1$H-NMR (δ ppm, CDCl$_3$) 7.49-6.97 (m, 4H), 4.71 (d, 1H, J=12.1 Hz), 4.49 (d, 1H, J=12.1 Hz), 3.74 (s, 3H), 3.71 (d, 1H, J=5.7 Hz), 2.18-2.00 (m, 1H), 0.96 (d, 3H, J=4.0 Hz), 0.92 (d, 3H, J=4.0 Hz); $^{13}$C-NMR (□ ppm, CDCl$_3$) 172.8, 163.1, 158.2, 130.3, 130.2, 129.5, 129.4, 124.0, 123.9, 115.3, 114.9, 83.6, 66.1, 66.0, 51.7, 31.6, 18.7, 17.7; [α]$_D^{25}$=−64.9 (c=1.27, CH$_2$Cl$_2$).

(S)-Methyl 2-(2,6-difluorobenzyloxy)-3-methylbutanoate. This compound was prepared from L-valine and 2,6-difluorobenzyl bromide in 51% yield: bp 78-80° C. (0.3 mm Hg); IR 1751, 1275 cm$^{-1}$; $^1$H-NMR (□ ppm, CDCl$_3$) 7.31-7.20 (m, 1H), 6.92-6.85 (m, 2H), 4.78 (db, 1H, J=11.3 Hz), 4.51 (d$_b$, 1H, J=11.3 Hz), 3.74 (s, 3H), 3.66 (d, 1 H, J=5.7 Hz), 2.01-1.98 (m, 1H), 0.97 (d, 3H, J=4.0 Hz), 0.95 (d, 3H, J=4.0 Hz); $^{13}$C-NMR (δ ppm, CDCl$_3$) 172.5, 164.4, 164.3, 159.4, 159.3, 130.5, 130.2, 130.0, 113.8, 113.2, 112.6, 111.3, 111.1, 110.9, 110.8, 83.2, 59.5, 51.4, 31.3, 18.3, 17.3; [α]$_D^{25}$=−70.2 (c=1.42, CH$_2$Cl$_2$).

(2S,3S)-Methyl 2-(benzyloxy)-3-methylpentanoate. This compound was prepared from L-isoleucine and benzyl bromide in 58% yield: bp 80-82° C. (0.8 mm Hg); IR 1750, 742, 700 cm$^{-1}$; $^1$H-NMR (δ ppm, CDCl$_3$) 7.35-7.25 (m, 5H), 4.67 (d, 1H, J=11.7 Hz), 4.36 (d, 1H, J=11.7 Hz), 3.75 (d, 1H, J=3.7 Hz), 3.73 (s, 3H), 1.92-1.76 (m, 1H), 1.68-1.47 (m, 1H), 1.35-1.13 (m, 1H), 0.90 (d, 3H, J=6.8 Hz), 0.85 (t, 3H, J=7.4 Hz); $^{13}$C-NMR (δ ppm, CDCl$_3$) 172.4, 137.3, 127.9, 127.5, 127.3, 82.1, 72.0, 51.0, 37.6, 24.3, 14.8,10.9; [α]$_D^{25}$=−66.7 (c=1.00, CH$_2$Cl$_2$).

(2S,3S)-Methyl 2-(3,5-difluorobenzyloxy)-3-methylpentanoate. This compound was prepared from L-isoleucine and 3,5-difluorobenzyl bromide in 63% yield: bp 78-80° C. (0.7 mm Hg); IR 1746, 1114, 850 cm$^{-1}$; $^1$H-NMR (δ ppm, CDCl$_3$) 6.90-6.66 (m, 3H), 4.64 (d, 1H, J=12.4 Hz), 4.33 (d, 1H, J=12.4 Hz), 3.78 (d, 1H, J=5.7 Hz), 3.76 (s, 3H), 2.01-1.79 (m, 1H), 1.65-1.44 (m, 1H), 1.40-1.13 (m, 1H), 0.96-0.85 (m, 6H); $^{13}$C-NMR (δ ppm, CDCl$_3$) 172.5, 165.5, 165.3, 160.6, 160.4, 142.0, 141.9, 141.7, 110.3, 110.1, 109.9, 109.8, 103.4, 102.9, 102.4, 83.1, 71.2, 51.7, 38.0, 24.6, 15.3, 11.3; [α]$_D^{25}$=−55.3 (c=1.10, CH$_2$Cl$_2$).

(2S,3S)-Methyl 2-(2,3-difluorobenzyloxy)-3-methylpentanoate. This compound was prepared from L-isoleucine and 2,3-difluorobenzyl bromide in 48% yield: bp 77-78° C. (0.3 mm Hg); IR 1744, 1287 cm$^{-1}$; $^1$H-NMR (δ ppm, CDCl$_3$) 7.25-7.03 (m, 3H), 4.70 (d, 1H, J=12.2 Hz), 4.48 (d, 1H, J=12.8 Hz), 3.78 (d, 1H, J=5.7 Hz), 3.75 (s, 3H), 1.93-1.77 (m, 1H), 1.59-1.42 (m, 1H), 1.36-1.13 (m, 1H), 0.92-0.82 (m, 6H); $^{13}$C-NMR (δ ppm, CDCl$_3$) 172.6, 152.9, 152.6, 151.1, 150.9, 148.0, 147.7, 146.2, 145.9, 127.4, 127.2, 124.9, 124.8, 124.7, 124.1, 124.0, 123.9, 116.8, 116.5, 83.2, 65.7, 65.6, 65.5, 51.7, 37.9, 24.6, 15.2, 11.3; [α]$_D^{25}$=−56.7 (c=0.40, CH$_2$Cl$_2$).

EXAMPLE 3

General Procedure for the Synthesis of α-Benzyloxy Aldehydes 5

A solution of lithium aluminum hydride (0.76 g, 20.0 mmol) in anhydrous ether (30 ml), under an inert atmosphere, was cooled to 0° C. The corresponding α-benzyloxy ester 4 (20.0 mmol) in anhydrous ether (40 ml) was added dropwise, and the mixture was stirred at room temperature for 3 h. Then, the reaction mixture was cooled in ice and treated with water (130 ml). The crude was filtrated through Celite, and the filtrate was washed with water (3×80 ml). The remaining organic layer was dried over Na$_2$SO$_4$ and evaporated under reduced pressure, providing the expected alcohol as an oil, which was purified by distillation under reduced pressure using a Kugelrohr. A solution of oxalyl chloride (1.82 ml, 21.0 mmol) in anhydrous methylene chloride (42 ml), under inert atmosphere, was cooled to −70° C. Anhydrous dimethyl sulfoxide (1.96 ml, 28.0 mmol) in anhydrous methylene chloride (42 ml) was added dropwise during 10 min. The temperature was maintained below −60° C. during the addition. To this mixture, the previously prepared and purified alcohol (14.0 mmol) dissolved in anhydrous methylene chloride (45 ml) was added dropwise during 10 min. The temperature was maintained below −60° C. during the addition. Then the mixture was stirred at −70° C. for 20 min. Triethylamine (7.84 ml, 56.0 mmol) was added dropwise during 5 min. The reaction was monitored by TLC. When the reaction was complete the mixture was allowed to reach room temperature. HCl 1N (56 ml, aqueous solution) and hexanes (140 ml) were added. The aqueous layer was separated and extracted twice with 90 ml aliquots of ether. The residual organic layer and ether extracts were combined and washed with NaHCO$_3$ saturated water solution (2×70 ml), water (2×70 ml) and brine (2×70 ml), dried over Na$_2$SO$_4$ and evaporated under reduced pressure providing an oily residue which was purified by distillation under reduced pressure using a Kugelrohr, yielding the corresponding aldehyde as a colorless oil.

(S)-2-(Benzyloxy)-3-methylbutanal. This compound was previously described by Jouillé et al. See: W.-R. Li, W. R. Ewing, B. D. Harris, M. M. Jouillé J. Am. Chem. Soc. 1990, 112, 7659.

(S)-2-(2-Fluorobenzyloxy)-3-methylbutanal. This compound was prepared from (S)-methyl 2-(2-fluorobenzyloxy)-3-methylbutanoate in 58% yield: bp 76-78° C. (0.3 mm Hg); IR 1732 cm$^{-1}$; $^1$H-NMR (δ ppm, CDCl$_3$) 9.66 (d, 1H, J=2.6 Hz), 7.48-7.09 (m, 4H), 4.72 (d, 1H, J=12.0 Hz), 4.56 (d, 1H, J=12.0 Hz), 3.59 (dd, 1H, J=5.7 Hz, J'=2.6 Hz), 2.18-2.01 (m, 1H), 0.99 (d, 3H, J=1.7 Hz), 0.96 (d, 3H, J=1.7 Hz); $^{13}$C-NMR (δ ppm, CDCl$_3$) 203.7, 162.9, 158.1, 130.1, 130.0, 129.6, 129.4, 123.9, 123.8, 115.2, 114.8, 88.2, 66.2, 29.7, 18.1, 17.2; [α]$_D^{25}$=−77.0 (c=1.51, CH$_2$Cl$_2$).

(S)-2-(2,6-Difluorobenzyloxy)-3-methylbutanal. This compound was prepared from (S)-methyl 2-(2,6-difluorobenzyloxy)-3-methylbutanoate in 73% yield: bp 75-76° C. (0.3 mm Hg); IR 1729, 1275 cm$^{-1}$; $^1$H-NMR (δ ppm, CDCl$_3$) 9.65 (d, 1H, J=2.7 Hz), 7.37-7.22 (m, 1H), 6.96-6.86 (m, 2H), 4.73 (d, 1H, J=11.0 Hz), 4.60 (d, 1H, J=11.0 Hz), 3.45 (dd, 1H, J=5.9 Hz, J'=2.7 Hz), 2.12-1.96 (m, 1H), 0.95 (d, 3H, J=2.0 Hz), 0.91 (d, 3H, J=2.0 Hz); $^{13}$C-NMR (δ ppm, CDCl$_3$) 204.1, 164.4, 164.2, 159.4, 159.3, 130.7, 130.6, 130.5, 113.6, 113.3, 111.5, 111.3, 111.2, 111.0, 88.5, 60.2, 60.1, 60.0, 29.8, 18.2, 17.3; [α]$_D^{25}$=−73.1 (c=1.14, CH$_2$Cl$_2$).

(2S,3S)-2-(Benzyloxy)-3-methylpentanal. This compound was prepared from (2S,3S)-methyl 2-(benzyloxy)-3-methylpentanoate in 88% yield: bp 67-68° C. (0.8 mm Hg); IR 1732 cm$^{-1}$; $^1$H-NMR (δ ppm, CDCl$_3$) 9.67 (d, 1H, J=2.8 Hz), 7.35-7.25 (m, 5H), 4.66 (d, 1H, J=11.7 Hz), 4.48 (d, 1H, J=11.7 Hz), 3.53 (t, 1H, J=2.9 Hz), 1.92-1.79 (m, 1H), 1.69-1.47 (m, 1H), 1.41-1.18 (m, 1H), 0.96-0.83 (m, 6H); $^{13}$C-NMR (δ ppm, CDCl$_3$) 204.0, 137.3, 128.2, 127.7, 87.0, 72.5, 36.2, 24.3, 14.8, 11.2; [α]$_D^{26}$=−84.5 (c=1.00, CH$_2$Cl$_2$).

(2S,3S)-2-(3,5-Difluorobenzyloxy)-3-methylpentanal. This compound was prepared from (2S,3S)-methyl 2-(3,5-difluorobenzyloxy)-3-methylpentanoate in 73% yield: bp 92-93° C. (0.5 mm Hg); IR 1734, 1113, 850 cm$^{-1}$; $^1$H-NMR (δ ppm, CDCl$_3$) 9.69 (d, 1H, J=2.5 Hz), 6.92-6.83 (m, 2H), 6.78-6.68 (m, 1H), 4.66 (d, 1H, J=12.5 Hz), 4.42 (d, 1H, J=12.5 Hz), 3.57 (dd, 1H, J=5.7, J'=2.5 Hz), 2.08-1.81 (m, 1H), 1.72-1.46 (m, 1H), 1.43-1.19 (m, 1H), 0.99 (d, 3H, J=6.9 Hz), 0.90 (d, 3H, J=7.4 Hz); $^{13}$C-NMR (δ ppm, CDCl$_3$) 203.3, 165.5, 165.3, 160.6, 160.3, 141.9, 141.7, 141.5, 110.1, 109.9, 109.8, 109.6, 103.4, 102.9, 102.4, 87.7, 71.2, 36.4, 24.5, 15.0, 11.3; [α]$_D^{25}$=−65.9 (c=1.00, CH$_2$Cl$_2$).

(2S,3S)-2-(2,3-Difluorobenzyloxy)-3-methylpentanal. This compound was prepared from (2S,3S)-methyl 2-(2,3-difluorobenzyloxy)-3-methylpentanoate in 85% yield: bp 88-89° C. (0.5 mm Hg); IR 1725, 1290 cm$^{-1}$; $^1$H-NMR (δ ppm, CDCl$_3$) 9.69 (d, 1H, J=2.5 Hz), 7.26-7.02 (m, 3H), 4.73 (dd, 1H, J=12.0 Hz, J'=1.0 Hz), 4.56 (dd, 1H, J=12.0 Hz, J'=1.0 Hz), 3.58 (dd, 1H, J=5.8, J'=2.5 Hz), 1.97-1.84 (m, 1H), 1.62-1.46 (m, 1H), 1.40-1.17 (m, 1H), 0.96 (d, 3H, J=6.9 Hz), 0.88 (d, 3H, J=7.4 Hz); $^{13}$C-NMR (δ ppm, CDCl$_3$) 203.3, 152.7, 152.4, 150.9, 150.7, 147.8, 147.5, 146.0, 145.7, 127.2, 126.9, 124.6, 124.5, 124.0, 123.9, 123.8, 116.7, 116.4, 87.7, 65.7, 36.2, 24.3, 14.7, 11.1; [α]$_D^{25}$=−64.7 (c=1.00, CH$_2$Cl$_2$).

EXAMPLE 4

General Procedure for the Synthesis of (E)-Nitroalkenes 6

A mixture of the corresponding aldehyde 5 (16.0 mmol), nitromethane (4.30 ml, 80.0 mmol) and triethylamine (0.32 ml, 2.28 mmol) was stirred at room temperature for 16 h. The excess of nitromethane was removed by evaporation under reduced pressure. The nitroaldol thus obtained as a mixture of diastereomers was dissolved in anhydrous methylene chloride (32 ml) and cooled to $-70°$ C. Methanesulfonyl chloride (1.48 ml, 19.11 mmol) was added dropwise followed by a solution of N,N-diisopropylethylamine (6.85 ml, 39.81 mmol) in dry methylene chloride (8 ml), keeping the reaction mixture below $-60°$ C. The mixture was stirred at $-70°$ C. for 2 h and then allowed to reach room temperature. The solution was washed with water (8 ml), HCl 1 N (4×8 ml, aqueous solution) and brine (8 ml), dried over $Na_2SO_4$ and evaporated. The product corresponding nitroalkene was purified by flash column chromatography as a pale yellow oil.

[[(S, E)-4Methyl-1-nitropent-1-en-3yloxy]methyl]benzene. This compound was obtained from (S)-2-(benzyloxy)-3-methylbutanal in 68% yield: b.p. 124-126° C. (0.2 mm Hg); IR 1527, 1348 $cm^{-1}$; $^1$H-NMR ($\delta$ ppm, $CDCl_3$) 7.47-7.28 (m, 6H), 7.21-7.06 (m, 2H), 4.58 (d, 1H, J=11.7 Hz), 4.43 (d, 1H, J=11.7 Hz), 3.86 (t, 1 H, J=5.2 Hz), 2.03-1.90 (m, 1H), 0.97 (d, 3H, J=6.8 Hz), 0.97 (d, 3H, J=6.8 Hz); $^{13}$C-NMR ($\delta$ ppm, $CDCl_3$) 140.7, 140.3, 138.4, 128.3, 127.7, 127.5, 80.0, 71.2, 17.9, 17.7; $[\alpha]_D^{25}$=−33.7 (c=2.30, $CH_2Cl_2$).

1-[[(S,E)-4Methyl-1-nitropent-1-en-3yloxy]methyl]-2-fluorobenzene. This compound was obtained from (S)-2-(2-fluorobenzyloxy)-3-methylbutanal in 81% yield: b.p. 110-111° C. (0.3 mm Hg); IR 1527, 1349, 1230 $cm^{-1}$; $^1$H-NMR ($\delta$ ppm, $CDCl_3$) 7.43-7.03 (m, 6H), 4.60 (d, 1H, J=11.7 Hz), 4.49 (d, 1H, J=11.7 Hz), 3.88 (t, 1H, J=5.3 Hz), 2.02-1.92 (m, 1 H), 0.94 ($t_b$, 3H, J=7.1 Hz); $^{13}$C-NMR ($\delta$ ppm, $CDCl_3$) 163.1, 158.2, 140.5, 140.4, 130.1, 130.0, 129.8, 129.7, 124.1, 124.0, 115.4, 115.0, 80.6, 65.6, 65.5, 32.5, 17.8; $[\alpha]_D^{25}$=−27.2 (c=1.03, $CH_2Cl_2$).

1-[[(S,E)-4Methyl-1-nitropent-1-en-3yloxy]methyl]-2,6-difluorobenzene. This compound was obtained from (S)-2-(2,6-difluorobenzyloxy)-3-methylbutanal in 95% yield: b.p. 110-111° C. (0.3 mm Hg); IR 1527, 1353, 1276 $cm^{-1}$; $^1$H-NMR ($\delta$ ppm, $CDCl_3$) 7.38-6.85 (m, 5H), 4.64 ($dt_b$, 1H, J=11.6 Hz, J'=1.4 Hz), 4.56 ($dt_b$, 1H, J=11.6 Hz, J'=1.4 Hz), 3.83 (dd, 1H, J=5.7 Hz, J'=3.7 Hz), 2.00-1.84 (m, 1H), 0.92 (d, 3H, J=4.7 Hz), 0.89 (d, 3H, J=4.7 Hz); $^{13}$C-NMR ($\delta$ ppm, $CDCl_3$) 164.2, 164.0. 159.2, 159.1, 140.4, 140.2, 130.6, 130.4, 130.2, 113.4, 113.1, 111.1, 111.0, 110.8, 80.5, 59.1, 59.0, 58.9, 32.4, 17.6, 17.4; $[\alpha]_D^{25}$=−40.5 (c=1.23, $CH_2Cl_2$).

[[(E,3S,4S)-4Methyl-1-nitrohex-1-en-3yloxy]methyl]benzene. This compound was obtained from (S)-2-(benzyloxy)-3-methylpentanal in 91% yield: b.p. 97-98° C. (0.9 mm Hg); IR 1526, 1344, 748, 697 $cm^{-1}$; $^1$H-NMR ($\delta$ ppm, $CDCl_3$) 7.35-7.07 (m, 7H), 4.56 (d, 1H, J=11.7 Hz), 4.44 (d, 1H, J=11.7 Hz), 3.96 (t, 1H, J=5.1 Hz), 1.91-1.72 (m, 1H), 1.63-1.41 (m, 1H), 1.32-1.10 (m, 1H), 0.92 (t, 3H, J=4.5 Hz), 0.88 (d, 3H, J=3.3 Hz); $^{13}$C-NMR ($\delta$ ppm, $CDCl_3$) 140.7, 140.3, 138.4, 128.3,127.7, 127.5, 80.0, 71.2, 17.9, 17.7; $[\alpha]_D^{25}$=−20.1 (c=1.00, $CH_2Cl_2$).

1-[[(E,3S,4S)-4Methyl-1-nitrohex-1-en-3yloxy]methyl]-3,5-difluorobenzene. This compound was obtained from (S)-2-(3,5-difluorobenzyloxy)-3-methylpentanal in 82% yield: b.p. 115-116° C. (0.3 mm Hg); IR 1522, 1344, 1113, 850 $cm^{-1}$; $^1$H-NMR ($\delta$ ppm, $CDCl_3$) 7.25-7.05 (m, 2H), 6.85-6.69 (m, 3H), 4.54 (d, 1H, J=12.6 Hz), 4.42 (d, 1H, J=12.6 Hz), 3.98 (t, 1H, J=5.1 Hz), 1.94-1.72 (m, 1H), 1.64-1.39 (m, 1H), 1.36-1.09 (m, 1H), 0.96-0.89 (m, 6H); $^{13}$C-NMR ($\delta$ ppm, $CDCl_3$) 165.5, 165.3, 160.6, 160.3, 141.8, 141.7, 141.5, 140.6, 140.0, 109.9, 109.7, 109.6, 109.4, 103.4, 102.9, 102.4, 79.6, 70.2, 38.9, 25.1, 14.2, 11.4; $[\alpha]_D^{25}$=−11.5 (c=1.00, $CH_2Cl_2$).

1-[[(E,3S,4S)-4Methyl-1-nitrohex-1-en-3yloxy]methyl]-2,3-difluorobenzene. This compound was obtained from (S)-2-(2,3-difluorobenzyloxy)-3-methylpentanal in 93% yield: b.p. 119-120° C. (0.6 mm Hg); IR 1530, 1352, 1104 $cm^{-1}$; $^1$H-NMR ($\delta$ ppm, $CDCl_3$) 7.26-7.05 (m, 5H), 4.61 (dd, 1H, J=12.0 Hz, J'=1.4 Hz), 4.52 (dd, 1H, J=12.0 Hz, J'=1.4 Hz), 3.99 (dd, 1H, J=5.5 Hz, J'=4.2 Hz), 1.91-1.68 (m, 1H), 1.63-1.37 (m, 1H), 1.33-1.08 (m, 1H), 0.94-0.85 (m, 6H); $^{13}$C-NMR ($\delta$ ppm, $CDCl_3$) 152.9, 152.7, 151.2, 150.9, 148.0, 147.8, 146.2, 146.0, 140.6, 140.2, 127.2, 126.9, 124.6, 124.5, 124.4, 124.3, 124.2, 124.1, 124.0, 117.1, 116.8, 79.8, 65.1, 65.0, 64.9, 38.9, 25.2, 14.4, 11.4; $[\alpha]_D^{25}$=−11.0 (c=1.10, $CH_2Cl_2$).

EXAMPLE 5

General Procedure for the Synthesis of Pyrrolidines 10

The imine 9 (5 mmol) was solved in $CH_3CN$ (50 ml), and then TEA (1.4 ml, 10 mmol), the nitroalkene 6 (5 mmol) and AgOAc (0.13 g, 0.75 mmol) were added. The progress of the reaction was monitored by TLC. After completion of the reaction, the mixture was filtered through a Celite pad and washed with $NH_4Cl$ saturated water solution (2×10 ml) and water (2×10 ml). After drying ($Na_2SO_4$), the solution was evaporated, and the crude mixture purified by flash chromatography (Ethyl acetate/hexanes). The resulting oily product was solved in DME (25 ml) and cooled down to 0° C. LiOH 1N aqueous solution (15 ml) was added dropwise, and the progress of the reaction was monitored by TLC. After completion of the reaction, citric acid 10% aqueous solution (15 ml, pH 6) was added. The resulting solution was extracted with $CH_2Cl_2$ (3×20 ml), and the combined organic fractions were dried and evaporated. The crude product was triturated in $Et_2O$ yielding the corresponding pyrrolidine 10 as a white solid.

(2S,3R,4S,5S)-3-[(S)-1-(Benzyloxy)-2-methypropyl]-4-nitro-5-phenyl-pyrrolidine-2-carboxylic acid (10a): 68% yield; mp 154-155° C. (dec.); IR 1734, 1551, 1364 $cm^{-1}$; $^1$H NMR ($\delta$ ppm, $CDCl_3$) 9.30 ($s_b$, 2H), 7.40-7.21 (m, 10H), 5.43 (d, 1H, J=5.8 Hz), 4.80 (d, 1H, J=5.8 Hz), 4.68 ($s_b$, 2H), 4.16 (d, 1H, J=7.4 Hz), 3.63 (d, 1H, J=6.5 Hz), 3.09 (d, 1H, J=7.4 Hz), 2.11-1.92 (m, 1H), 0.97 (d, 3H, J=6.7 Hz), 0.88 (d, 3H, J=6.7 Hz); $^{13}$C NMR ($\delta$ ppm, $CDCl_3$) 173.2, 138.5, 135.8, 128.4, 128.2, 128.0, 127.6, 126.7, 91.8, 83.1, 73.5, 67.0, 62.7, 51.5, 30.9, 18.4. Anal. Calcd. for $C_{22}H_{26}N_2O_5$: C, 66.30; H, 6.59; N, 7.03. Found: C, 65.89; H, 6.64; N, 7.02%; $[\alpha]_D^{25}$=+33.0 (c=1.04, $CH_2Cl_2$).

(2S,3R,4S,5S)-5-tert-Butyl-3-[(S)-1-(benzyloxy)-2-methypropyl]-4-nitropyrrolidine-2-carboxylic acid (10b): 55% yield; mp 155-157° C. (dec.); IR 1734, 1551, 1364 $cm^{-1}$; $^1$H NMR ($\delta$ ppm, $CDCl_3$) 10.35 ($s_b$, 2H), 7.42-7.25 (m, 5H), 5.09 (d, 1H, J=4.6 Hz), 4.81 (d, 1H, J=10.2 Hz), 4.60 ($d_b$, 2H, J=4.9 Hz), 4.56 (d, 1H, J=10.2 Hz), 3.72 (d, 1H, J=4.6 Hz), 3.62 (tb, 1H, J=4.0 Hz), 3.05-2.95 (m, 1H), 2.10-1.90 (m, 1H), 1.10-0.85 (m, 15H); $^{13}$C NMR ($\delta$ ppm, $CDCl_3$) 172.3, 138.2, 128.4, 127.8, 86.5, 85.1, 74.5, 70.1, 63.5, 50.8, 32.2, 31.5, 26.5, 19.0, 17.7. Anal. Calcd. for $C_{20}H_{30}N_2O_5$: C, 63.45; H, 8.00; N, 7.40. Found: C, 62.91; H, 7.94; N, 7.44%; $[\alpha]_D^{25}$=+33.0 (c=1.04, $CH_2Cl_2$).

(2S,3R,4S,5S)-3-[(S)-1-(2-Fluorobenzyloxy)-2-methypropyl]-4-nitro-5-phenyl-pyrrolidine-2-carboxylic acid (10c): 66% yield; mp 158-159° C. (dec.); IR 1734, 1551, 1364 $cm^{-1}$; $^1H$ NMR (δ ppm, $CDCl_3$) 7.47-6.70 (m, 11H), 5.39 (dd, 1H, J=6.1 Hz, J'=1.7 Hz), 4.80-4.66 (m, 3H), 4.06 (d, 1H, J=7.2 Hz), 3.62 ($d_b$, 1H, J=6.8 Hz), 3.13 ($d_b$, 1H, J=7.4 Hz), 2.15-1.95 (m, 1H), 1.01 (d, 3H, J=6.7 Hz), 0.89 (d, 3H, J=6.7 Hz); $^{13}C$ NMR (δ ppm, $CDCl_3$) 173.3, 163.4, 158.5, 132.8, 130.6, 130.5, 130.2, 130.0, 128.8, 126.2, 124.9, 124.6, 124.4, 124.3, 115.7, 115.3, 90.5, 84.5, 68.4, 6.3, 66.7, 63.0, 51.6, 31.5, 19.0, 18.4. Anal. Calcd. for $C_{22}H_{25}N_2O_5F$: C, 63.44; H, 6.06; N, 6.73. Found: C, 62.96; H, 6.07; N, 6.72%; $[\alpha]_D^{25}$=+22.4 (c=1.13, $CH_2Cl_2$).

(2S,3R,4S,5S)-3-[(1S,2S)-1-(Benzyloxy)-2-methylbutyl]-4-nitro-5-phenyl-pyrrolidine-2-carboxylic acid (10d): 71% yield; mp 162-164° C. (dec.); IR 3435, 1627, 1555, 1377 $cm^{-1}$; $^1H$ NMR (δ ppm, $CDCl_3$) 7.37-7.22 (m, 10H), 5.69 ($s_b$, 2H), 5.43 (dd, 1H, J=6.2 Hz, J'=1.8 Hz), 4.76 (d, 1H, J=11.3 Hz), 4.71 (d, 1H, J =6.7 Hz), 4.54 (d, 1H, J=11.3 Hz), 3.94 (d, 1H, J=7.0 Hz), 3.74 (d, 1H, J=5.2 Hz), 3.09 ($d_b$, 1H, J=7.2 Hz), 1.94-1.78 (m, 1H), 1.57-1.39 (m, 1H), 1.28-1.05 (m, 1H), 0.96-0.85 (m, 6H); $^{13}C$ NMR (δ ppm, $CDCl_3$) 173.3, 137.9, 133.2, 128.8, 128.6, 128.1, 127.8, 126.2, 90.8, 82.9, 73.4, 67.1, 63.4, 51.1, 37.4, 26.0, 14.5, 11.7. Anal. Calcd. for $C_{23}H_{28}N_2O_5$: C, 66.96; H, 6.85; N, 6.79. Found: C, 66.78; H, 6.82; N, 6.72%; $[\alpha]_D^{25}$=+52.2 (c=0.60, $CH_2Cl_2$).

(2S,3R,4S,5S)-3-[(S)-1-(2,6-Difluorobenzyloxy)-2-methypropyl]-4-nitro-5-phenyl-pyrrolidine-2-carboxylic acid (10e): 60% yield; mp 169-170° C.; IR 1734, 1551, 1364 $cm^{-1}$; $^1H$ NMR (δ ppm, $CDCl_3$) 7.40-7.20 (m, 6H), 7.00-6.86 (m, 2H), 5.39 ($s_b$, 2H), 5.28 (dd, 1H, J=6.2 Hz, J'=1.8 Hz), 4.89 (d, 1H, J=10.5 Hz), 4.66 ($d_b$, J=6.9 Hz), 3.88 (d, 1H, J=6.8 Hz), 3.57 (dd, 1H, J=7.1 Hz, J'=1.3 Hz), 3.15 ($d_b$, 1H, J=7.4 Hz), 2.18-1.98 (m, 1H), 1.09 (d, 3H, J=6.7 Hz), 0.93 (d, 3H, J=6.7 Hz); $^{13}C$ NMR (δ ppm, $CDCl_3$) 173.7, 164.3, 164.1, 159.3, 159.2, 133.1, 130.9, 130.6, 130.4, 128.7, 126.2, 113.4, 112.3, 111.8, 111.6, 111.4, 111.3, 90.7, 84.4, 66.9, 63.1, 61.5, 61.4, 51.9, 31.6, 18.8, 18.5. Anal. Calcd. for $C_{22}H_{24}N_2O_5F_2$: C, 60.81; H, 5.58; N, 6.45. Found: C, 60.15; H, 5.49; N, 6.54%; $[\alpha]_D^{25}$=+25.9 (c=1.00, $CH_2Cl_2$).

(2S,3R,4S,5S)-3-[(1S,2S)-1-(Benzyloxy)-2-methylbutyl]-5-cyclohexyl-4-nitropyrrolidine-2-carboxylic acid (10f): 55% yield; mp 194-196° C.; IR 3437, 1635, 1553, 1380 $cm^{-1}$; $^1H$ NMR (δ ppm, $CDCl_3$) 7.40-7.29 (m, 5H), 5.23 (d, 1H, J =4.9 Hz), 4.73 (d, 1H, J=10.4 Hz), 4.57 (d, 1H, J=10.4 Hz), 4.33 (d, 1H, J=7.1 Hz), 3.72 (d, 1H, J=5.5 Hz), 3.55 (dd, 1H, J=4.9 Hz, J'=3.9 Hz), 2.99 (d, 1H, J=6.0 Hz), 2.04-2.01 (m, 1H), 1.83-1.41 (m, 8H), 1.32-1.13 (m, 5H), 0.99-0.85 (m, 7H); $^{13}C$ NMR (□ ppm, $CDCl_3$) 172.1, 138.3, 128.6, 128.5, 128.0, 87.8, 84.1, 74.2, 67.3, 64.0, 50.7, 38.0, 36.8, 30.3, 30.2, 25.8, 25.7, 24.8, 14.8, 11.9. Anal. Calcd. For $C_{23}H_{34}N_2O_5$: C, 65.99; H, 8.20; N, 6.69. Found: C, 65.79; H, 8.10, N, 6.83%; $[\alpha]_D^{25}$=+51.0 (c=1.0, $CH_2Cl_2$).

(2S,3R,4S,5S)-3-[(1S,2S)-1-(3,5-Difluorobenzyloxy)-2-methylbutyl]-4-nitro-5-phenyl-pyrrolidine-2-carboxylic acid (10g): 69% yield; mp 146-147° C. (dec.); IR 3428, 1626, 1555, 1378, 1119 $cm^{-1}$; $^1H$ NMR (δ ppm, $CDCl_3$) 7.43-7.26 (m, 5H), 7.09-6.68 (m, 3H), 5.46 (dd, 1H, J=5.9 Hz, J'=2.0 Hz), 4.75 (d, 1H, J=5.9 Hz), 4.67 (d, 1H, J=11.7 Hz), 4.60 (d, 1H, J=11.7 Hz), 4.13 (d, 1H, J=8.2 Hz), 3.75 (d, 1H, J=6.1Hz), 3.06 ($d_b$, 1H, J=7.9 Hz), 1.94-1.70 (m, 1H), 1.55-1.30 (m, 1H), 1.28-0.97 (m, 1H), 0.92-0.78 (m, 6H); $^{13}C$ NMR (δ ppm, $CDCl_3$) 172.6, 165.6, 165.4, 160.7, 160.4, 141.9, 141.8, 141.6, 131.5, 129.0, 125.9, 110.7, 110.5, 110.4, 110.2, 103.7, 103.2, 102.7, 90.1, 83.0, 72.3, 65.9, 63.1, 51.1, 37.5, 25.7, 14.3, 11.6. Anal. Calcd. for $C_{23}H_{26}N_2O_5F_2$: C, 61.59; H, 5.86; N, 6.25. Found: C, 61.60; H, 5.89; N, 6.19%; $[\alpha]_D^{25}$=+21.4 (c=0.80, $CH_2Cl_2$).

(2S,3R,4S,5S)-3-[(1S,2S)-1-(Benzyloxy)-2-methylbutyl]-5-cyclopropyl-4-nitro-pyrrolidine-2-carboxylic acid (10h): 39% yield; mp 159-161° C.; IR 3248, 1557, 1389 $cm^{-1}$; $^1H$ NMR (δ ppm, $CDCl_3$) 7.32-7.27 (m, 5H), 5.19 (d, 1H, J=4.9 Hz), 4.65 (d, 1H, J=10.4 Hz), 4.50 (d, 1H, J=10.2 Hz), 4.21 (d, 1H, J=4.3 Hz), 3.70 (d, 1H, J=5.4 Hz), 3.10 (m, 2H), 1.79-1.68 (m, 1H), 1.52-1.42 (m, 1H), 1.14-1.03 (m, 1H), 0.90-0.78 (m, 6H), 0.79-0.66 (m, 2H), 0.66-0.54 (m, 2H), 0.29-0.19 (m, 1H); $^{13}C$ NMR (□ ppm, $CDCl_3$) 172.3, 138.4, 128.8, 128.6, 128.2, 89.2, 83.8, 74.2, 67.9, 63.7, 50.8, 38.1, 30.0, 25.9, 14.9, 12.1, 7.8, 4.4, 1.4. Anal. Calcd. For $C_{20}H_{28}N_2O_5$: C, 63.81; H, 7.51; N, 7.44. Found: C, 63.99; H, 7.60, N, 7.50%; $[\alpha]_D^{25}$=+37.8 (c=0.86, $CH_3OH$).

(2S,3R,4S,5S)-3-[(1S,2S)-1-(2,3-Difluorobenzyloxy)-2-methylbutyl]-4-nitro-5-phenyl-pyrrolidine-2-carboxylic acid (10i): 58% yield; mp 148-149° C. (dec.); IR 3428, 1626, 1555, 1386, 1287 $cm^{-1}$; $^1H$ NMR (δ ppm, $CDCl_3$) 8.23 ($s_b$, 2H) 7.30-7.05 (m, 8H), 5.43 (dd, 1H, J=6.0 Hz, J'=1.8 Hz), 4.80-4.65 (m, 3H), 4.06 (d, 1H, J=7.6 Hz), 3.76 (d, 1H, J=6.0 Hz), 3.05 ($d_b$, 1H, J=7.8 Hz), 1.92-1.77 (m, 1H), 1.53-1.33 (m, 1H), 1.25-1.06 (m, 1H), 0.92-0.82 (m, 6H); $^{13}C$ NMR (6 ppm, $CDCl_3$) 172.8, 152.9. 152.7, 151.3, 151.1, 148.0, 147.8, 146.4, 146.1, 131.8, 128.9, 127.4, 127.1, 125.9, 125.2, 125.1, 125.0, 124.4, 124.3, 124.2, 117.2, 116.9, 90.3, 83.1, 66.6, 66.3, 63.4, 51.1, 37.4, 25.6, 14.3, 11.6. Anal. Calcd. for $C_{23}H_{26}N_2O_5F_2$: C, 61.59; H, 5.86; N, 6.25. Found: C, 61.57; H, 5.87; N, 6.25%; $[\alpha]_D^{25}$=+26.4 (c=0.77, $CH_2Cl_2$).

(2S,3S,4S,5S)-3-[(1S,2S)-1-(Benzyloxy)-2-methylbutyl]-2-methyl-4-nitro-5-phenyl-pyrrolidine-2-carboxylic acid (10j): 83% yield; mp 98-99° C. (dec.); IR 3438, 1725, 1640, 1551, 1362 $cm^{-1}$; $^1H$ NMR (δ ppm, $CDCl_3$) 7.39-7.25 (m, 10H), 5.51 (dd, 1H, J=6.4 Hz, J'=2.5 Hz), 5.36 ($s_b$, 2H), 4.78 (d, 1H, J=6.9 Hz), 4.72 (d, 1H, J=11.2 Hz), 4.41 (d, 1H, J=11.2 Hz), 3.82 (d, 1H, J=3.8 Hz), 3.17 (d, 1H, J=2.2 Hz), 2.08-1.93 (m, 1H), 1.65 (s, 3H), 1.32-1.14 (m, 1H), 1.13-0.98 (m, 1H), 0.91 (t, 3H, J=7.1Hz), 0.81 (d, 3H, J=6.9 Hz); $^{13}C$ NMR (δ ppm, $CDCl_3$) 176.0, 134.0, 131.7, 128.7, 128.4, 127.7, 127.4, 126.3, 90.7, 79.5, 70.5, 69.6, 64.3, 51.2, 36.2, 25.8, 18.7, 13.4, 12.0. Anal. Calcd. for $C_{24}H_{30}N_2O_5$: C, 67.57; H, 7.10; N, 6.57. Found: C, 66.94; H, 7.19; N, 6.56%; $[\alpha]_D^{25}$=+9.9 (c=0.53, $CH_2Cl_2$).

(2S,3R,4S,5S)-3-[(1S,2S)-1-(benzyloxy)-2-methylbutyl]-5-[(S)-1-(benzyloxy)-2-methylpropyl]-4-nitropyrrolidine-2-carboxylic acid (10k): 20% yield; mp 172-174° C.; IR 3428, 1635, 1555, 1386 $cm^{-1}$; $^1H$ NMR (□ ppm, $CDCl_3$) 7.88 ($s_b$, 2H), 7.35-7.23 (m, 10H), 5.24 (d, 1H, J=4.8 Hz), 4.65 (d, 1H, J=10.3 Hz), 4.55 (d, 1H, J=10.4 Hz), 4.51 (d, 1H, J=11.1Hz), 4.37 (d, 1H, J=11.1Hz), 4.22 (d, 1H, J=6.1Hz), 3.94 (t, 1H, J=5.7 Hz, J'=5.6 Hz), 3.65 (d, 1H, J=5.9 Hz), 3.52 (t, 1H, J=5.1Hz, J'=5.7 Hz), 2.94 (d, 1H, J=6.1Hz), 2.12-2.09 (m, 1H), 1.84-1.75 (m, 1H), 1.54-1.48 (m, 1H), 1.16-1.07 (m, 1H), 0.89-0.85 (m, 12H); $^{13}C$ NMR (□ ppm, $CDCl_3$) 172.9, 138.2, 137.9, 128.7, 128.2, 128.0, 87.0, 84.5, 82.2, 75.3, 74.4, 65.0, 64.3, 51.6, 38.1, 31.0, 26.0, 19.8, 17.3, 15.0, 11.0, 2.3. Anal. Calcd. For $C_{28}H_{38}N_2O_6$: C, 67.45; H, 7.70; N, 5.62. Found: C, 67.23; H, 7.51, N, 5.57%; $[\alpha]_D^{25}$=+14.6 (c =1.1, $CH_2Cl_2$).

EXAMPLE 6

General Procedure for the Synthesis of Compounds 11

To a round bottom flask under argon atmosphere, the cycloadduct 10 (1 mmol) and glycine hydrochloride methyl ester (1 mmol) in 2.5 ml of anhydrous DMF were introduced, and the mixture was cooled with an ice/water bath. DECP (0.18 ml, 1.2 mmol) in 0.5 ml of DMF and TEA (0.29 ml, 2.05 mmol) were added dropwise, and the resulting mixture was stirred at room temperature for 16 hours. Then AcOEt (100 ml) and toluene (100 ml) were added, and the organic solution was washed with 50 ml fractions of $H_2O$, $Na_2S_2O_3$ 1N aqueous solution, $H_2O$, $NaHCO_3$ saturated aqueous solution and NaCl saturated aqueous solution, dried ($Na_2SO_4$) and evaporated. The crude mixture was purified by flash chromatography (Ethyl acetate/hexanes). The resulting oily product was solved in DME (5 ml) and cooled down to 0° C. LiOH 1 N aqueous solution (3 ml) was added dropwise, and the progress of the reaction was monitored by TLC. After completion of the reaction, citric acid 10% aqueous solution (3 ml, pH 6) was added. The resulting solution was extracted with $CH_2Cl_2$ (3×4 ml), and the combined organic fractions were dried and evaporated. The crude product was triturated in $Et_2O$ yielding the corresponding product 11 as a white solid.

2-[(2S,3R,4S,5S)-3-[(S)-1-(Benzyloxy)-2-methylpropyl]-4-nitro-5-phenylpyrrolidine-2-carboxamido]acetic acid (11a): 68% yield; mp 71-72° C.; IR 1736, 1641, 1545, 1368 $cm^{-1}$; $^1H$ NMR (δ ppm, $CDCl_3$) 7.71 ($t_b$, 1H, J=5.1Hz), 7.43-7.22 (m, 10H), 5.51 ($s_b$, 2H), 5.33 (dd, 1H, J=6.6 Hz, J'=2.3 Hz), 4.80 (d, 1H, J=11.6 Hz), 4.59 (d, 1H, J=6.6 Hz), 4.58 (d, 1H, J=11.6 Hz), 4.14 (m, 2H), 3.77 (d, 1H, J=7.4 Hz), 3.59 (d, 1H, J=6.5 Hz), 3.18 ($d_b$, 1H, J=7.4 Hz), 2.10-1.92 (m, 1H), 1.01 (d, 3H, J=6.8 Hz), 0.87 (d, 3H, J=6.8 Hz); $^{13}C$ NMR (δ ppm, $CDCl_3$) 173.1, 173.0, 138.2, 134.7, 128.8, 128.6, 127.9, 127.6, 126.6, 90.7, 84.1, 74.1, 66.8, 63.2, 50.8, 41.1, 31.4, 19.2, 18.3. Anal. Calcd. for $C_{24}H_{29}N_3O_6$: C, 63.27; H, 6.43; N, 9.23. Found: C, 62.87; H, 6.39; N, 9.23%; $[\alpha]_D^{25}$=+30.7 (c=0.88, $CH_2Cl_2$).

2-[(2S,3R,4S,5S)-5-tert-Butyl-3-[(S)-1-(benzyloxy)-2-methylpropyl]-4-nitropyrrolidine-2-carboxamido]acetic acid (11b): 76% yield; mp 119-120° C.; IR 3367, 3283, 1707, 1693, 1555, 1377 $cm^{-1}$; $^1H$ NMR (δ ppm, $CDCl_3$) 7.56 ($t_b$, 1H, J=4.9 Hz), 7.40-7.25 (m, 5H), 5.08 (d, 1H, J=5.3 Hz), 4.74 (d, 1H, J=11.2 Hz), 4.49 (d, 1H, J=11.2 Hz), 4.12 (dd, 1H, J=19.5 Hz, J'=4.9 Hz), 4.00 (dd, 1H, J=19.5 Hz, J'=4.9 Hz), 3.85 (d, 1H, J=6.3 Hz), 3.49 (dd, 1H, J=6.0 Hz, J'=1.5 Hz), 3.14 (d, 1H, J=5.3 Hz), 2.93 (d, 1H, J=6.3 Hz), 2.06-1.95 (m, 1H), 1.01-0.88 (m, 6H), 0.90 (s, 9H); $^{13}C$ NMR (δ ppm, $CDCl_3$) 173.2, 171.8, 138.0, 128.5, 127.9, 127.6, 86.5, 85.0, 74.3, 73.1, 63.2, 51.6, 41.8, 32.4, 31.4, 26.5, 19.0, 18.4. Anal. Calcd. for $C_{22}H_{33}N_3O_6$: C, 60.66; H, 7.65; N, 9.65. Found: C, 60.61; H, 7.70; N, 9.78%; $[\alpha]_D^{25}$=+10.0 (c=1.00, $CH_2Cl_2$).

2-[(2S,3R,4S,5S)-3-[(S)-1-(2-Fluorobenzyloxy)-2-methylpropyl]-4-nitro-5-phenyl-pyrrolidine-2-carboxamido]acetic acid (11c): 65% yield; mp 72-73° C.; IR 3378, 3330, 1741, 1665, 1550, 1363, 1225 $cm^{-1}$; $^1H$ NMR (δ ppm, $CDCl_3$) 7.82 ($t_b$, 1H, J=5.4 Hz), 7.79-7.02 (m, 9H), 6.00 ($s_b$, 2H), 5.29 (dd, 1H, J=6.6 Hz, J'=2.3 Hz), 4.77 (d, 1H, J=11.1 Hz), 4.70 (d, 1H, J=11.2 Hz), 4.61 (d, 1H, J=6.6 Hz), 4.20 (dd, 1H, J=18.3 Hz, J'=5.4 Hz), 4.08 (dd, 1H, J=18.3 Hz, J'=5.4 Hz), 3.85 (d, 1H, J=7.3 Hz), 3.59 ($d_b$, 1H, J=4.8 Hz), 3.19 ($d_b$, 1H, J=7.3 Hz), 2.10-1.90 (m, 1H), 1.02 (d, 3H, J=6.9 Hz), 0.86 (d, 3H, J=6.9 Hz); $^{13}C$ NMR (δ ppm, $CDCl_3$) 173.2, 173.0, 163.4, 158.5, 134.8, 130.4, 130.3, 130.1, 129.9, 128.8, 128.6, 126.6, 125.2, 124.9, 124.3, 124.2, 115.7, 115.3, 90.7, 84.4, 68.4, 68.3, 66.8, 63.2, 50.8, 41.1, 31.5, 19.1, 18.3. Anal. Calcd. for $C_{24}H_{28}N_3O_6F$: C, 60.86; H, 5.97; N, 8.87. Found: C, 60.14; H, 6.03; N, 8.75%; $[\alpha]_D^{25}$=+25.3 (c=0.66, $CH_2Cl_2$).

2-[(2S,3R,4S,5S)-3-[(1S,2S)-1-(Benzyloxy)-2-methylbutyl]-4-nitro-5-phenyl-pyrrolidine-2-carboxamido]acetic acid (11d): 78% yield; mp 156-157° C.; IR 3368, 3321, 1737, 1669, 1545, 1363 $cm^{-1}$; $^1H$ NMR (δ ppm, $CDCl_3$) 7.70 ($t_b$, 1H, J=5.2 Hz), 7.38-7.25 (m, 10H), 6.39 ($s_b$, 2H), 5.37 (dd, 1H, J=6.8 Hz, J'=2.4 Hz), 4.78 (d, 1H, J=11.5 Hz), 4.61 (d, 1H, J=6.4 Hz), 4.54 (d, 1H, J=11.4 Hz), 4.19 (dd, 1H, J=18.4 Hz, J'=3.1 Hz), 4.09 (dd, 1H, J=18.2 Hz, J'=2.9 Hz), 3.78 (d, 1H, J=7.6 Hz), 3.73 (d, 1H, J=5.9 Hz), 3.16 ($d_b$, 1H, J=8.4 Hz), 1.97-1.73 (m, 1H), 1.59-1.36 (m, 1H), 1.27-1.01 (m, 1H), 0.95-0.83 (m, 6H); $^{13}C$ NMR (δ ppm, $CDCl_3$) 173.1, 172.9, 138.1, 134.6, 128.9, 128.6, 127.9, 127.6, 126.6, 90.8, 82.4, 73.1, 66.9, 63.5, 50.2, 41.1, 37.2, 25.9, 14.4, 11.7. Anal. Calcd. for $C_{25}H_{31}N_3O_6$: C, 63.99; H, 6.67; N, 8.96. Found: C, 63.94; H, 6.56; N, 9.05%; $[\alpha]_D^{25}$=+39.2 (c=0.60, $CH_2Cl_2$).

2-[(2S,3R,4S,5S)-3-[(S)-1-(2,6-Difluorobenzyloxy)-2-methylpropyl]-4-nitro-5-phenyl-pyrrolidine-2-carboxamido]acetic acid (11e): 65% yield; mp 80-81° C.; IR 3372, 3334, 1734, 1635, 1555, 1358, 1275 $cm^{-1}$; $^1H$ NMR (δ ppm, $CDCl_3$) 7.82 ($t_b$, 1H, J=4.0 Hz), 7.36-7.22 (m, 6H), 6.97-6.87 (m, 2H), 5.22 (dd, 1H, J=6.6 Hz, J'=2.4 Hz), 4.86 (d, 1H, J=10.4 Hz), 4.68 (d, 1H, J=10.4 Hz), 4.59 (d, 1H, J=6.6 Hz), 4.24 (dd, 1H, J=18.2 Hz, J'=4.0 Hz), 4.15 ($s_b$, 2H), 4.14 (dd, 1H, J=18.2 Hz, J'=4.0 Hz), 3.84 (d, 1H, J=7.5 Hz), 3.58 (d, 1H, J=6.3 Hz), 3.18 ($d_b$, 1H, J=8.0 Hz), 2.10-1.88 (m, 1H), 1.02 (d, 3H, J=6.7 Hz), 0.86 (d, 3H, J=6.8 Hz); $^{13}C$ NMR (δ ppm, $CDCl_3$) 173.2, 173.0, 164.3, 164.2, 159.4, 159.2, 135.0, 130.7, 130.5, 130.3, 128.7, 128.5, 126.7, 114.0, 113.6, 113.2, 111.7, 111.5, 111.4, 111.2, 90.6, 84.5, 66.7, 63.2, 61.4, 50.9, 41.1, 31.6, 19.0, 18.4. Anal. Calcd. for $C_{24}H_{27}N_3O_6F_2$: C, 58.64; H, 5.55; N, 8.55. Found: C, 58.47; H, 5.52; N, 8.53%; $[\alpha]_D^{25}$=+23.2 (c=1.02, $CH_2Cl_2$).

2-[(2S,3R,4S,5S)-3-[(1S,2S)-1-(benzyloxy)-2-methylbutyl]-5-cyclohexyl-4-nitropyrrolidine-2-carboxamido]acetic acid (11f): 55% yield; mp 177-179° C.; IR 3377, 3286, 1678, 1552, 1387 $cm^{-1}$; $^1H$ NMR (δ ppm, DMSO-$d_6$) 12.63 ($s_b$, 1H), 8.33 (t, 1H, J=5.8 Hz), 7.43-7.32 (m, 5H), 5.21 (s, 1H), 4.71 (d, 1H, J=11.5 Hz), 4.63 (d, 1H, J=11.5 Hz), 3.92-3.82 (m, 2H), 3.65 (d, 1H, J=5.3 Hz), 3.49 (d, 1H, J=7.5 Hz), 2.93 (s, 1H), 2.82 (d, 1H, J=7.6 Hz), 1.88-1.75 (m, 3H), 1.68-1.60 (m, 3H), 1.46-1.38 (m, 1H), 1.22-0.94 (m, 7H), 0.90 (t, 3H, J=7.3 Hz), 0.82 (d, 3H, J=6.9 Hz); $^{13}C$ NMR (δ ppm, DMSO-$d_6$) 172.5, 138.5, 128.9, 128.3, 128.0, 88.9, 83.1, 73.6, 69.8, 64.2, 51.6, 41.8, 38.4, 37.8, 31.0, 30.8, 30.1, 26.3, 25.7, 25.5, 14.9, 12.1, 2.3. Anal. Calcd. For $C_{25}H_{37}N_3O_6$: C, 63.12; H, 7.86; N, 8.84. Found: C, 62.90; H, 7.68, N, 8.59%; $[\alpha]_D^{25}$=+16.6 (c=0.80, $CH_3OH$).

2-[(2S,3R,4S,5S)-3-[(1S,2S)-1-(3,5-Difluorobenzyloxy)-2-methylbutyl]-4-nitro-5-phenylpyrrolidine-2-carboxamido]acetic acid (11g): 77% yield; mp 140-141° C.; IR 3466, 3381, 1734, 1687, 1555, 1386, 1122 $cm^{-1}$; $^1H$ NMR (δ ppm, $CDCl_3$) 7.81 ($t_b$, 1H, J=5.3 Hz), 7.33-7.25 (m, 5H), 6.90-6.70 (m, 3H), 6.18 ($s_b$, 2H), 5.36 (dd, 1H, J=5.7 Hz, J'=1.9 Hz), 4.74 (d, 1H, J=12.0 Hz), 4.60 (d, 1H, J=7.3 Hz), 4.55 (d, 1H, J=12.0 Hz), 4.17 (d, 2H, J=5.3 Hz), 3.82 (d, 1H, J=7.5 Hz), 3.76 (d, 1H, J=6.1 Hz), 3.21 ($d_b$, 1H, J=7.2 Hz), 1.95-1.70 (m, 1H), 1.63-1.41 (m, 1H), 1.33-1.06 (m, 1H), 0.91 (t, 3H, J=7.0 Hz), 0.83 (d, 3H, J=6.9 Hz); $^{13}C$ NMR (δ ppm, $CDCl_3$) 173.1, 173.0, 165.6, 165.4, 160.7, 160.4, 142.3, 142.1, 142.0, 134.5, 128.9, 128.6, 126.6, 110.0, 109.8, 109.7, 109.5, 103.5, 103.0, 102.5, 90.6, 83.0, 71.8, 67.0, 63.5, 50.0, 41.1, 37.2, 25.9, 14.3, 11.7. Anal. Calcd. for $C_{25}H_{29}N_3O_6F_2$: C, 59.39; H, 5.79; N, 8.31. Found: C, 58.87; H, 5.81; N, 8.27%; $[\alpha]_D^{25}=+29.7$ (c=0.69, $CH_2Cl_2$).

2-[(2S,3R,4S,5S)-3-[(1S,2S)-1-(benzyloxy)-2-methylbutyl]-5-cyclopropyl-4-nitropyrrol-idine-2-carboxamido] acetic acid (11h): 46% yield; mp 161-163° C.; IR 3356, 1673, 1562, 1399 cm$^{-1}$; $^1$H NMR (□ ppm, DMSO-d$_6$) 12.64 (s$_b$, 1H), 8.25 (t, 1H, J=5.8 Hz), 7.41-7.31 (m, 5H), 5.17 (dd,1H, J=4.2 Hz, J'=4.2 Hz), 4.68 (d,1H, J=11.6 Hz), 4.62 (d, 1H, J=11.6 Hz), 3.91-3.82 (m, 2H), 3.63 (dd, 1H, J=1.8 Hz, J'=1.9 Hz), 3.46 (d, 1H, J=8.3 Hz), 3.04-3.03 (m, 1H), 2.69 (t, 1H, J=7.7 Hz), 1.79-1.69 (m, 1H), 1.47-1.39 (m, 1H), 1.13-1.04 (m, 1H), 0.90 (t, 3H, J=7.3 Hz), 0.80 (d, 3H, J=6.9 Hz), 0.64-0.58 (m, 1H), 0.51-0.39 (m, 2H), 0.34-0.26 (m, 2H); $^{13}$C NMR (□ ppm, DMSO-d$_6$) 172.8, 171.9, 139.5, 129.2, 128.1, 91.3, 82.3, 73.5, 68.6, 64.5, 52.1, 41.5, 37.7, 26.0, 15.5, 12.4, 11.0, 3.7, 3.1. Anal. Calcd. For $C_{22}H_{31}N_3O_6$: C, 60.95; H, 7.22; N, 9.70. Found: C, 61.23; H, 7.35, N, 9.76%; $[\alpha]_D^{25}=+24.6$ (c=0.56, $CH_2Cl_2$).

2-[(2S,3R,4S,5S)-3-[(1S,2S)-1-(2,3-Difluorobenzyloxy)-2-methylbutyl]-4-nitro-5-phenylpyrrolidine-2-carboxamido]acetic acid (11i): 67% yield; mp 137-138° C.; IR 3371, 1734, 1682, 1565, 1376, 1295 cm$^{-1}$; $^1$H NMR (δ ppm, CDCl$_3$) 7.79 (t$_b$, 1H, J=5.8 Hz), 7.36-7.09 (m, 8H), 5.32 (dd, 1H, J=5.8 Hz, J'=2.5 Hz), 4.78 (d, 1H, J=11.2 Hz), 4.67 (d, 1H, J=11.2 Hz), 4.60 (d, 1H, J=6.8 Hz), 4.19 (d, 2H, J=5.8 Hz), 3.81 (d, 1H, J=7.9 Hz), 3.78 (d, 1H, J=6.4 Hz), 3.54 (s$_b$, 2H), 3.20-3.16 (m, 1H), 1.92-1.76 (m, 1H), 1.57-1.38 (m, 1H), 1.28-1.06 (m, 1H), 0.93 (t, 3H, J=7.2 Hz), 0.84 (d, 3H, J=6.9 Hz); $^{13}$C NMR (δ ppm, CDCl$_3$) 173.2, 173.1, 153.1, 152.8, 151.4, 151.2, 148.1, 147.9, 146.5, 146.2, 134.7, 128.9, 128.6, 127.6, 127.3, 126.7, 124.9, 124.8, 124.7, 124.4, 124.2, 124.1, 117.3, 117.0, 90.7, 82.9, 66.9, 63.5, 50.1, 41.0, 37.2, 25.9, 14.4, 11.7. Anal. Calcd. for $C_{25}H_{29}N_3O_6F_2$: C, 59.39; H, 5.79; N, 8.31. Found: C, 58.83; H, 5.81; N, 8.39%; $[\alpha]_D^{25}=+40.4$ (c=0.50, $CH_2Cl_2$).

2-[(2S,3R,4S,5S)-3-[(1S,2S)-1-(Benzyloxy)-2-methylbutyl]-2-methyl-4-nitro-5-phenyl-pyrrolidine-2-carboxamido]acetic acid (11j): 72% yield; mp 89-90° C.; IR 3381, 3306, 1748, 1668, 1551, 1367 cm$^{-1}$; $^1$H NMR (δ ppm, CDCl$_3$) 8.27 (t$_b$, 1H, J=3.6 Hz), 7.44-7.23 (m, 10H), 5.46 (dd, 1H, J=6.8 Hz, J'=2.9 Hz), 5.28-5.60 (s$_b$, 2H), 4.75 (d, 1H, J=6.8 Hz), 4.70 (d, 1H, J=11.2 Hz), 4.41 (d, 1H, J=11.2 Hz), 4.15 (d, 1H, J=3.6 Hz), 3.82 (d, 1H, J=4.0 Hz), 3.22 (d, 1H, J=2.9 Hz), 2.09-1.83 (m, 1H), 1.58 (s, 3H), 1.49-1.23 (m, 1H), 1.21-0.98 (m, 1H), 0.91 (t, 3H, J=7.2 Hz), 0.76 (d, 3H, J=7.0 Hz); $^{13}$C NMR (δ ppm, CDCl$_3$) 176.7, 138.3, 135.7, 128.7, 128.4, 128.1, 127.5, 127.1, 126.9, 104.1, 91.4, 79.7, 70.3, 66.1, 64.9, 50.3, 35.9, 29.6, 26.1, 18.9, 13.3, 11.9. Anal. Calcd. for $C_{26}H_{33}N_3O_6$: C, 64.57; H, 6.89; N, 8.69. Found: C, 64.25; H, 6.95; N, 8.65%; $[\alpha]_D^{25}=+2.1$ (c=0.96, $CH_2Cl_2$).

2-[(2S,3R,4S,5S)-3-[(1S,2S)-1-(benzyloxy)-2-methylbutyl]-5-[(S)-1-(benzyloxy)-2-methylpropyl]-4-nitropyrrolidine-2-carboxamido]acetic acid (11k): 44% yield; mp 153-155° C.; IR 3417, 1678, 1547, 1387 cm$^{-1}$; $^1$H NMR (□ppm, CDCl$_3$) 7.50-7.01 (m, 11H), 5.68 (s$_b$, 2H), 5.27 (s, 1H), 4.71 (d, 1H, J=10.6 Hz), 4.50 (d, 1H, J=10.8 Hz), 4.40 (d, 1H, J=10.9 Hz), 4.33 (d, 1H, J=10.6 Hz), 4.13-3.90 (m, 2H), 3.67 (d, 1H, J=5.5 Hz), 3.59-3.41 (m, 2H), 3.33 (d, 1H, J=3.6 Hz), 2.92 (d, 1H, J=2.1 Hz), 2.03-1.94 (m, 1H), 1.87-1.77 (m, 1H), 1.56-1.50 (m, 1H), 1.23-1.12 (m, 2H), 1.06-0.74 (m, 11H); $^{13}$C NMR (□ ppm, CDCl$_3$) 172.7, 172.6, 138.5, 138.4, 129.0, 128.7, 128.3, 128.2, 128.0, 88.1, 84.1, 83.1, 74.8, 74.0, 66.8, 65.0, 52.0, 41.7, 38.0, 30.9, 26.3, 19.9, 17.4, 15.0, 12.0. Anal. Calcd. For $C_{30}H_{41}N_3O7$: C, 64.85; H, 7.45; N, 7.56. Found: C, 64.97; H, 7.66, N, 7.64%; $[\alpha]_D^{25}=+8.7$ (c=0.30, $CH_2Cl_2$).

EXAMPLE 7

In Vitro Biological Activity Studies

To determine which of the compounds synthesized possesses a greater ability to serve as a VLA-4 antagonist, a discriminatory procedure is performed based on an in vitro test of the adhesion of tumor cells to single layers of the HSE in primary culture treated or untreated with TNF-α to stimulate VCAM-1 expression. The tumor used is the B16F10 subline of MB16, the VLA-4 expression of which is constitutive.

B16 (MB16) Melanoma Cell Culture

The MB16 tumor cells (subline B16F10) are cultured in incubator at 37° C., with 5% CO2 atmosphere, in DMEM medium (Dulbecco's modified Eagle's medium), adjusted to pH 7.4 and supplemented with penicillin (100 U/ml), streptomycin (100 µg/ml) and 5% fetal bovine serum. The cells are maintained and subcultured according to a previously-described method (Vidal-Vanaclocha et al. Cancer Research, 1994, 54, 2667).

Isolation and Primary Culture of Hepatic Sinusoid Endothelial Cells (HSE)

The hepatic sinusoidal cells are isolated from C57BU6J mice (males, age 6-8 weeks) supplied by IFFA Credo (L'Arbreole, France). For their purification and identification, the previously-described protocol is employed (Vidal-Vanaclocha et al. Hepatology, 1993, 18, 328-339). The primary HSE cell cultures are obtained by seeding the cells on a Type I collagen substrate (Sigma Chemicals Co, St Louis, Mo.) in the presence of DMEM, supplementing with penicillin (100 U/ml), streptomycin (100 µg/ml) and 10% fetal bovine serum, at 37° C. in 5% CO2 atmosphere.

MB16 Cell Adhesion to the Single Layer of HSE Cells in Culture

The endothelial cells are isolated 24 hours prior to the adhesion test and are seeded on 24-well plate, maintaining them a minimum of 4 hours in free serum medium before incubating them with DMEM in the presence or not of 10 ng/ml TNF-α for 6 hours. The B16 cells are marked with 40 µg/ml of the BCECF-AM fluorescent probe (carboxyfluorescein, 2',7'-bis-(2-carboxy-etyl)-5-(6)carboxyfluorescein aminoxymethyl ester), supplied by Molecular Probes Inc. (Oregon, USA). Afterward, a washing with DMEM medium without serum is performed to remove the excess flurochromium, and the compounds of general formula I are incubated at 37° C. for 15 minutes at the concentration of 50 µg/1×106 MB16 cells. This is followed by two washings, the number of visible cells being calculated by means of the trypan blue dye exclusion test, and they are resuspended to a concentration of 2×105 cells/ml. One (1) ml of the MB16 cell suspension is added to each well on the primary HSE cell culture plate, and the co-cultures are incubated at 37° C. for 8 minutes. The percentage of cellular adhesion is calculated by means of a previously-described fluorescence measurement system (Vidal-Vanaclocha et al. Cancer Research, 1994, 54, 2667).

To prove that the anti-adhesive effect of the le compound is due to the blocking of the VLA-4NCAM-1 binding, tests are conducted on MB16 adhesion to recombinant human VCAM-1 substrates immobilized on 96-well plated. The incubation of MB16 with increasing concentrations of the le compound decreases the adhesion thereof to VCAM-1, this inhibiting effect even being found in MB16 cells preincubated with 1 ng/ml of IL-18 recombinant murine for 6 hours for increasing the VLA-4 the expression thereof.

EXAMPLE 8

In-Vitro Anti-Metastatic Activity Studies

A description is provided in following of the effect of the le compound on the metastatic capacity of MB16 in in-vivo tests. For this purpose, the MB16 cells treated with le are inoculated intrasplenically in C57BU6J mice ($3 \times 10^5$ viable cells per animal, resuspended in endotoxin-free sterile saline solution), and the microvascular retention within the first 18 hours and their ability to develop metastasis on day 12 following the tumor injection is determined.

The blocking of tumoral VLA-4 following the preincubation of MB16 cells with the le compound reduces their intrahepatic retention by 50% 18 hours following their inoculation. These retention experiments are conducted with MB16 cells transfected with the luciferase gene, according to a previously-described protocol (Mendoza et al. Hepatology, 2001, 34, 298).

Likewise, the inhibition figures achieved with le for intrahepatic retention and the formation of metastasis of B16 melanoma tally with the inhibition of the same parameters obtained following the preincubation of the melanoma with anti-VLA-4 antibodies or the prior intravenous administration of anti-VCAM-1 murine antibodies in animals receiving a B16 melanoma cell injection. (Anasagasti et al. Hepatology 1997;25:840-846; Mendoza et al. Hepatology 2001 ;34:298).

Figure 6:
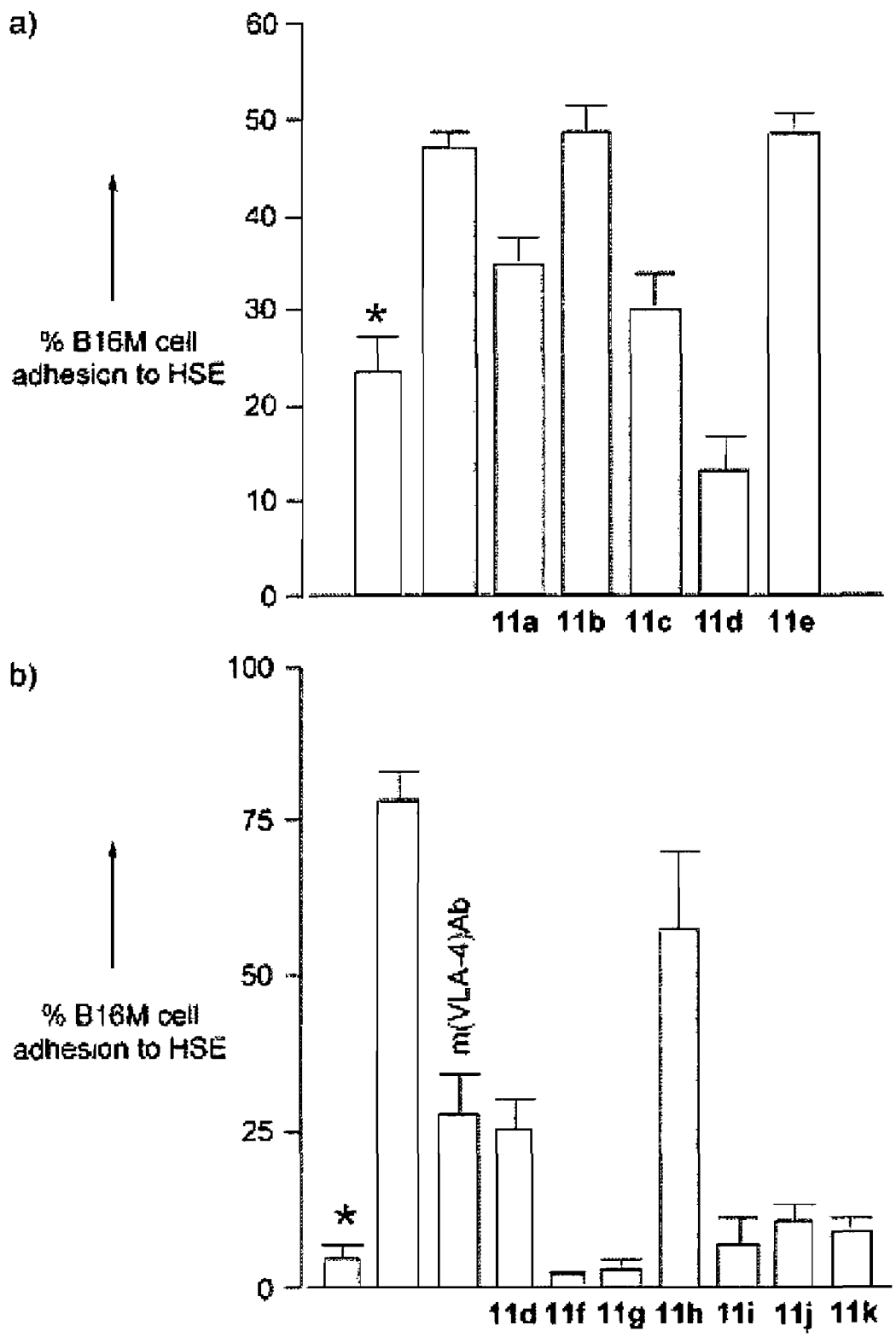
FIG. 6 shows the anti-adhesive properties of inhibitors 11.

Next, the potential VLA-4 antagonism of compounds 11 was tested through a previously established model on VLA-4NCAM-1-interaction-dependent B16M cell adhesion to primary cultured hepatic sinusoidal endothelial (HSE) cells in vitro. As shown in FIG. 6, both B16M cell adhesion to TNF-alpha-treated HSE cells which increases VCAM-1 expression on endothelial cells and $H_2O_2$-treated B16M cell adhesion to unstimulated HSE cells which increases VLA-4 activation in cancer cells significantly increased relative to their respective untreated control cells ($P<0.01$, where P is the statistical probability value). Preincubation of B16M cells with compounds 11 and measurement of adhesion to HSE resulted in variable responses as shown in FIG. 6. Interestingly, compounds 11b and 11h with tBu and cPr groups at R3, respectively, did not show any significant antiadhesive activity. Similarly, compound 11e, with a 2,6-difluorophenyl group at $R^2$ and a methyl group at $R^1$ was also almost inactive. In contrast, the presence of a quaternary atom at the a-position of the pyrrolidine ring (R4=Me), such as in 11j, did not result in a significant loss of activity.

Figure 3:
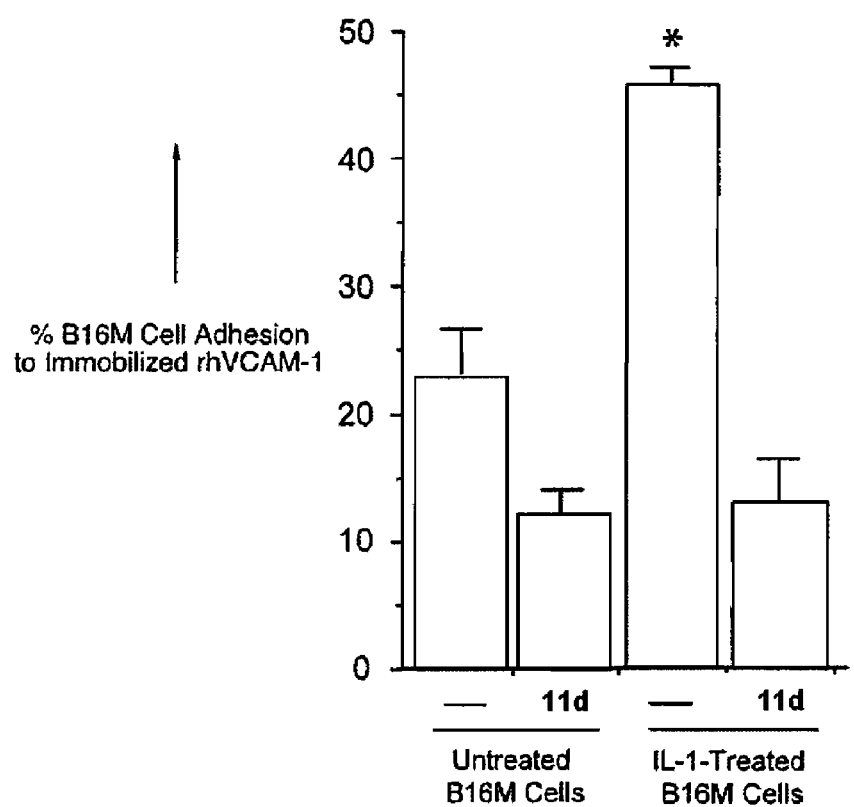
FIG. 3 shows the effect of compound 11d on the adhesion of untreated and interleukin-18 (IL-18)-treated B16M cells to immobilized VCAM-1 in vitro.
Figure 4:
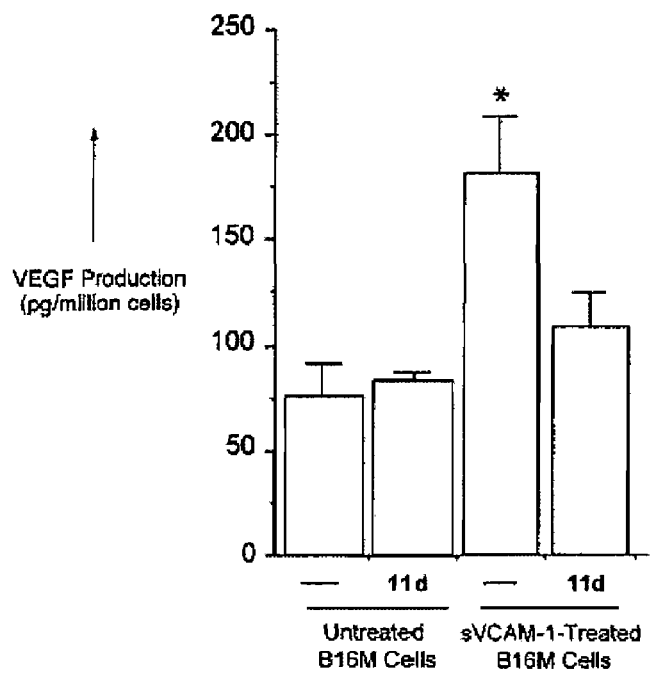
FIG. 4 shows the effect of compound 11d on vascular endothelial growth factor (VEGF) production by untreated and soluble VCAM-1-treated B16M cells in vitro.
Figure 7:
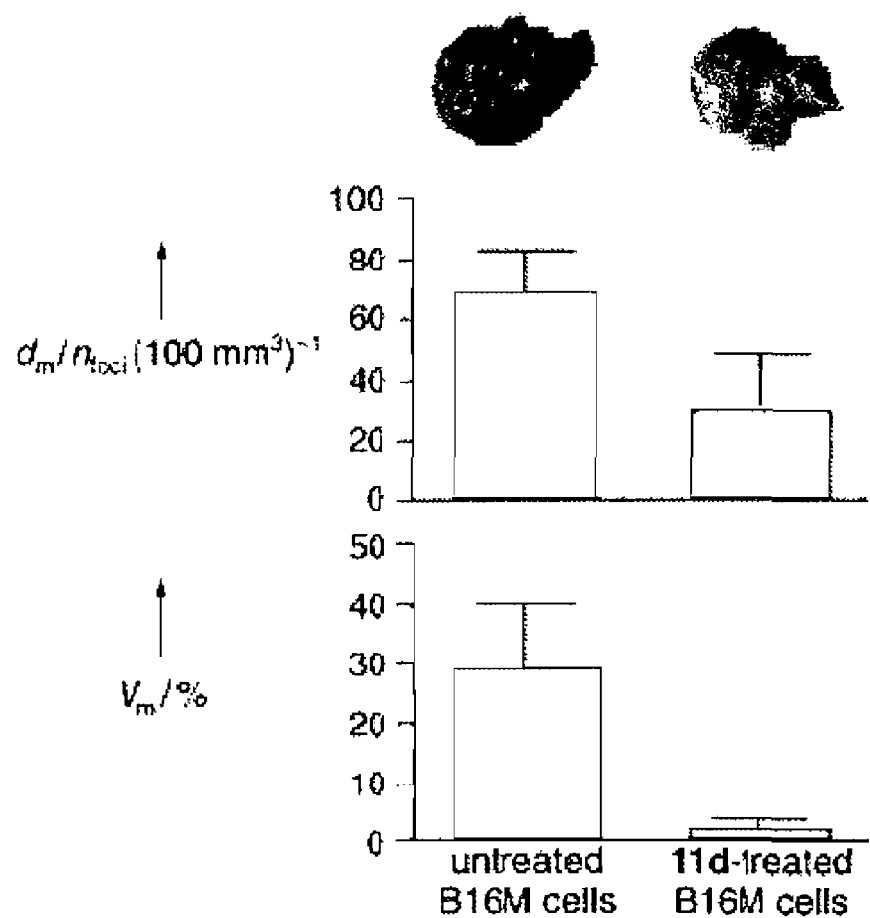
FIG. 7 shows the antimetastatic activity of compound 11d on male C57BU6J mice.

Although the best activity in vitro was shown by compound 11f, which has a cyclohexyl group at R3, preliminary assays in vivo were carried out with 11d (R3=Ph) because of its higher solubility in water. Additionally, 11d displayed comparable antiadhesive activity to monoclonal antibodies against murine VLA-4 (FIG. 6B). Furthermore, addition of 11d compound to IL-1b (interleukin-1b)-treated melanoma cells completely abrogated their adhesion to immobilized VCAM-1 (FIG. 3) and prevented vascular endothelial growth factor (VEGF) production induced by soluble VCAM-1-stimulated cells (FIG. 4), which confirms the potent VLA-4 antagonism of compound 11d. Finally, metastasis density and volume significantly decreased ($P<0.01$) by 60% and 95%, respectively, in mice that were intrasplenically injected with 11d-pretreated B16M cells relative to those that received untreated cells (FIG. 7). B16M cells were cultured for 24 hours in the presence 50 μg/ml of compound 11d, or 5 pg/ml anti-murine VLA-4 antibody. Cultured cells were fixed and processed for the immunohistochemical detection of Ki-67 antigen expression. Next, a computed-aid microscopic image analysis system was used to discriminate stained cells (brown nuclei) and calculate the average number of Ki-67 antigen-expressing cells per $1 \times 10^4$ cells. The results are the mean±SD of 6 independent fields, from 3 different experiments (n=18).

Parallel measurements on cell viability and cytotoxicity, intracellular oxidative metabolism, and cell-proliferation rates of 11d-treated melanoma cells excluded that antimetastatic effects of 11d compound may have been caused by indirect effects on cell functions other than those specifically operated through a VLA-4-dependent mechanism.

EXAMPLE 9

In-Vivo and In Vitro Anti-Inflammatory and Anti-Angiogenic Effects

Figure 8:
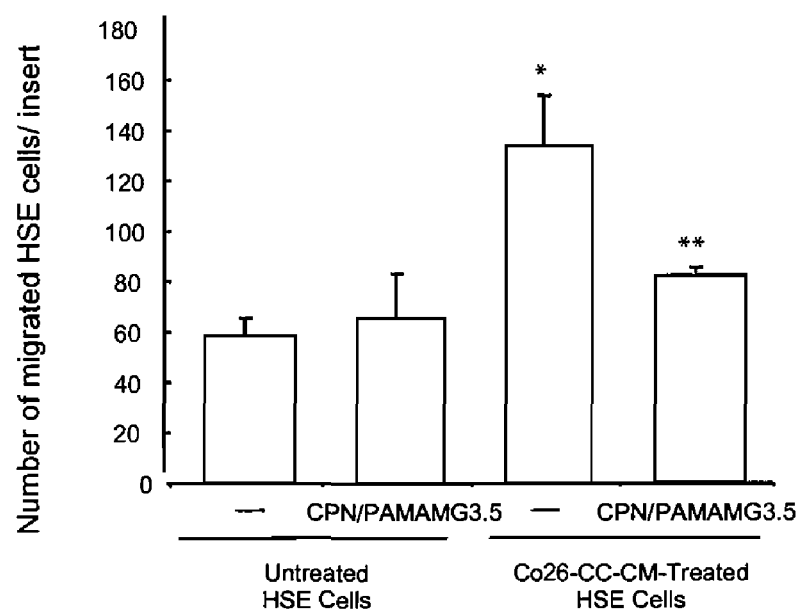
FIG. 8 shows that Synthetic VLA-4 Inhibitor (CPN/PAMAM-G3.5) Inhibits tumoral soluble factors-induced Endothelial Cell Migration. HSE cells were placed in the upper compartment of a modified Boyden chamber and incubated with basal medium or Co26-CC-CM in the presence or absence of 25 μg/ml CPN/PAMAM-G3.5. The lower compartment contained basal medium. After 48 hours, migrated cells were analyzed. Differences in the number of migrated cells with respect to untreated HSE cells (*) or Co26-CC-CM-treated HSE cells (**) were statistically significant (P<0.01), by ANOVA and Bonferroni's post-hoc test. Conditioned media from Co26 colon carcinoma cells (Co26-CC-CM) induced HSE migration through collagen type 1. This effect was completely neutralized by the addition of CPN/PAMAM-G3.5.
Figure 9:
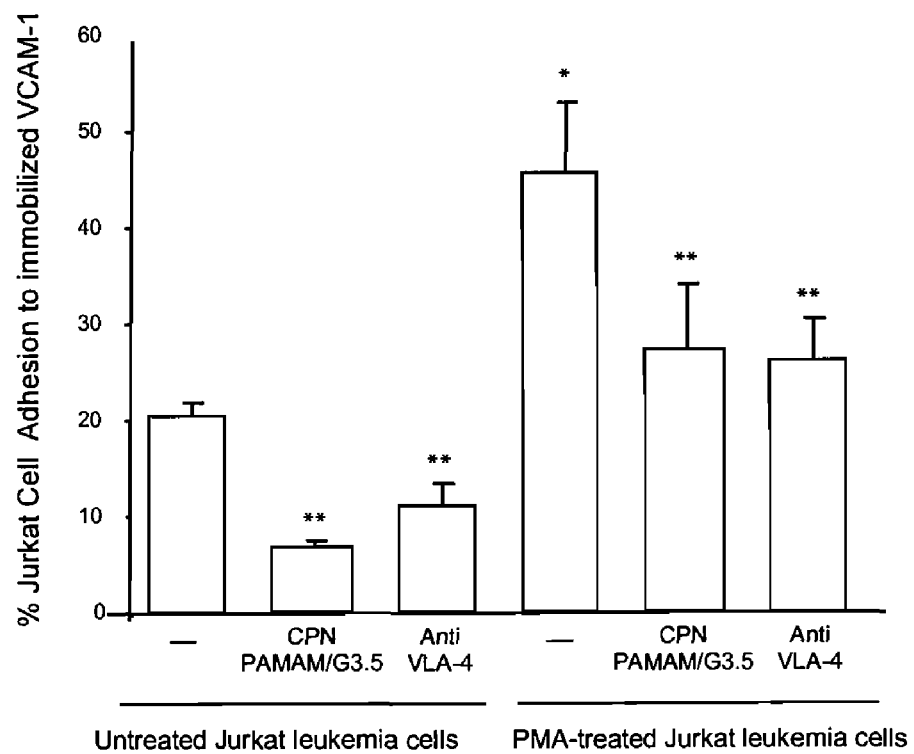
FIG. 9 shows that VLA-4 Inhibitor CPN/PAMAM-G3.5 Inhibits Jurkat Leukemia Cell adhesion to Immobilized VCAM-1. Ninety six-well plates are coated with 2 μg/ml recombinant human VCAM-1 (R&D Systems, Minneapolis, Minn.) at 4° C. overnight. Nonspecific binding sites on plastic are blocked by treating the wells with 100 μl of PBS containing 0.5% BSA for 2 h at room temperature. Jurkat leukemia cells are incubated with either basal medium or 100 ng/ml PMA for 30 min. Then, cells are BCECF-AM-labeled and after washing, the compound CPN/PAMAMG3.5 (50 μg/1×10$^6$ cells) is added for 30 min. For adhesion assay, Jurkat cells (1×10$^5$ per well) are added to quadruplicate wells. Then, plates are incubated for 45 minutes at 37° C. before unattached cells are removed by washing three times with fresh medium. The number of adhering cells is determined using a quantitative fluorescence measurement system. Differences in the percent of adhering Jurkat cells with respect to (*) untreated cells or (**) PMA-treated cells, were statistically significant (P<0.01) by ANOVA and Bonferroni's post-hoc test.

The potential anti-inflammatory effects of VLA-4 antagonism of compounds 11 was tested in adhesion assays of human peripheral blood-derived lymphocytes and Jurkat leukemia cells to immobilized VCAM-1 substrate. Ninety six-well plates are coated with 2 μg/ml recombinant human VCAM-1 (R&D Systems, Minneapolis, Minn.) at 4° C. overnight. Nonspecific binding sites on plastic are blocked by treating the wells with 100 μl of PBS containing 0.5% BSA for 2 h at room temperature. Isolated peripheral blood human lymphocytes are incubated with either basal medium or 100 ng/ml PMA for 30 min. Then, lymphocytes are BCECF-AM-labeled and after washing, the compound CPN/PAMAMG3.5 (50 μg/$1 \times 10^6$ cells) is added for 30 min. For adhesion assay, lymphocytes ($1 \times 10^5$ per well) are added to quadruplicate wells. Then, plates are incubated for 1 hour at 37° C. before unattached cells are removed by washing three times with fresh medium. The number of adhering cells is determined using a quantitative fluorescence measurement system. Differences in the percent of adhering lymphocytes with respect to (*) untreated cells or (**) PMA-treated cells, were statistically significant ($P<0.01$) by ANOVA and Bonferroni's post-hoc test. As shown in FIG. 8, compound CPN/PAM-AMG3.5 almost completely abrogated the adhesion of PMA-treated lymphocytes to VCAM-1 substrate. Comparable effects were obtained with PMA-treated Jurkat leukemia cells (FIG. 9).

Figure 10:
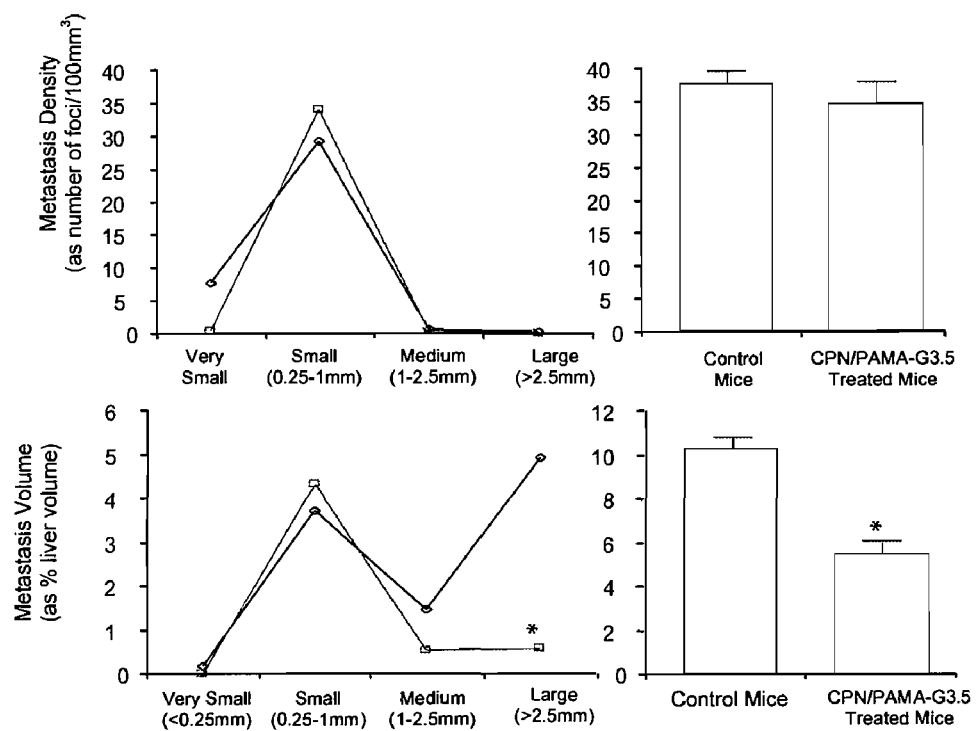
FIG. 10 shows that Treatment with Synthetic VLA-4 Inhibitor (CPN/PAMAM-G3.5) Reduces Metastatic Growth of Intrasplenically-Injected Co26 Colon Carcinoma Cells. Balb/c mice were intrasplenically injected with 18×10$^4$ Co26 colon carcinoma cells n=10/group). They were killed on day 12 and their livers were processed for histological analyses. Metastatic foci were arbitrarily subdivided in four groups attending to their average diameter: (very small: 0-0.25 mm; small: 0.25-1; medium: 1-2.5 mm; and large: >2.5 mm) and their separate average densities and the percentage of liver volume occupied by metastatic foci were calculated. The histograms represent the average values of the experiment. *Differences in average values of metastasis volume were statistically significant with respect to control mice (P<0.01) according by t'Student test. VLA-4 Inhibitor Treatment Schedule: VLA-4 synthetic inhibitor was mixed with PAMAM-G3.5 macromolecule in a 1:4 ratio (CPN/PAMAM-G3.5). First, mice were given one intraperitoneal injection of either PAMAM-G3.5 or CPN/PAMAM-G3.5 (2.5 mg/kg) 1 hour prior cancer cell inoculation and then, the same dose was repeated on days 2,3,8,9,10 and 11 postinjection.
Figure 11:
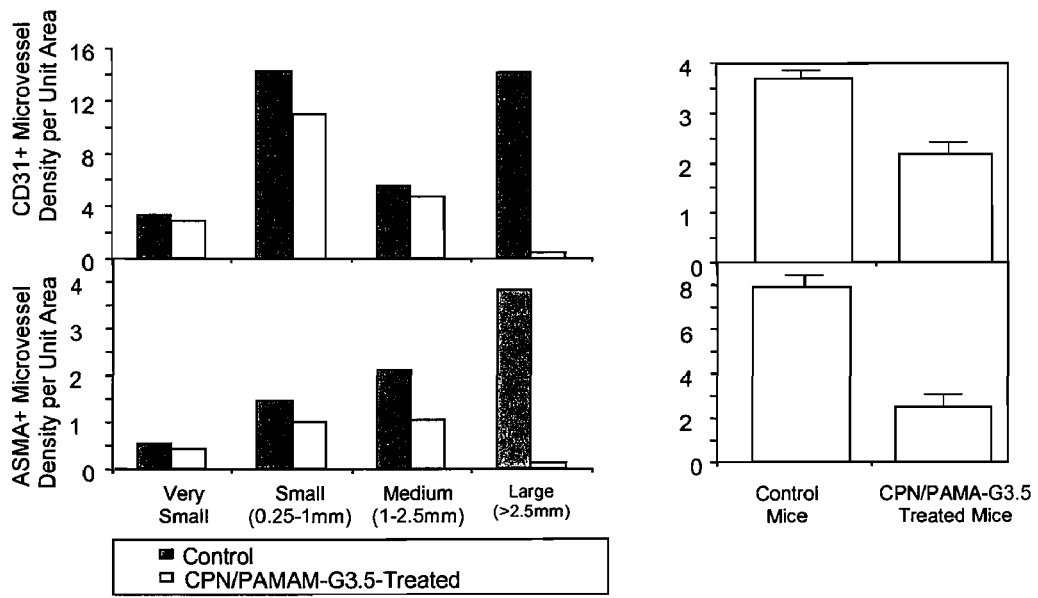
FIG. 11 shows that VLA-4 Inhibitor CPN/PAMAM-G3.5 Treatment Inhibits Endothelial cell and myofibroblast Recruitment into Co26 Colon Carcinoma Cell Hepatic Metastases. Microvessel density per surface unit of metastatic tissue was determined by morphometrical study of densitometrically discriminated CD31-expressing and ASMA-expressing microvessels. Both parameters were separately analyzed in metastases with different size from PAMA-G3.5- and CPN/PAMA-G3.5-treated mice. The histograms represent the average values of the experiment.
Figure 12:
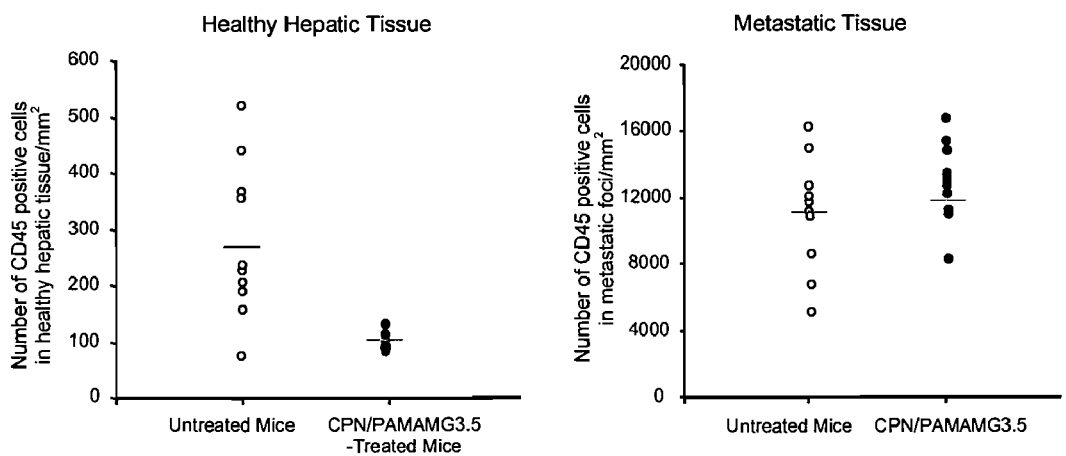
FIG. 12 shows that Immunohistochemical characterization of inflammatory infiltrates demonstrates that VLA-4 inhibitor treatment Inhibits leucocyte recruitment into healthy hepatic tissue and not into metastatic tissue. Leucocyte recruitment was determined by morphometrical study of CD45-expressing cell number in liver sections.
Figure 13:
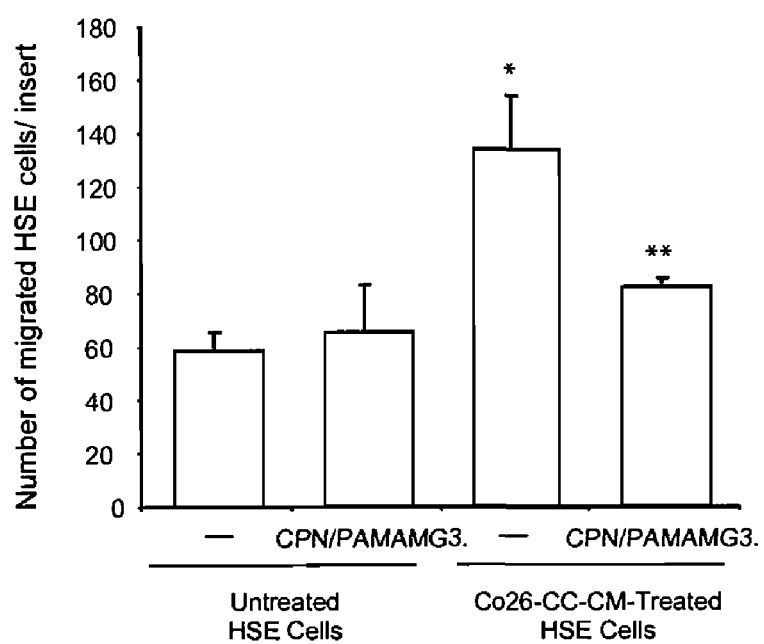
FIG. 13 shows that Synthetic VLA-4 Inhibitor (CPN/PAMAM-G3.5) Inhibits tumoral soluble factors-induced Endothelial Cell Migration. HSE cells were placed in the upper compartment of a modified Boyden chamber and incubated with basal medium or Co26-CC-CM in the presence or absence of 25 μg/ml CPN/PAMAM-G3.5. The lower compartment contained basal medium. After 48 hours, migrated cells were analyzed. Differences in the number of migrated cells with respect to untreated HSE cells (*) or Co26-CC-CM-treated HSE cells (**) were statistically significant (P<0.01), by ANOVA and Bonferroni's post-hoc test. Conditioned media from Co26 colon carcinoma cells (Co26-CC-CM) induced HSE migration through collagen type 1. This effect was completely neutralized by the addition of CPN/PAMAM-G3.5.

Next, the effect of VLA-4 antagonists was tested in an experimental model of hepatic colonization of a murine colon carcinoma cells. Balb/c mice were intrasplenically injected with $18 \times 10^4$ Co26 colon carcinoma cells n=10/group). They were killed on day 12 and their livers were processed for histological analyses. Metastatic foci were arbitrarily subdivided in four groups attending to their average diameter: (very small: 0-0.25 mm; small: 0.25-1; medium: 1-2.5 mm; and large: >2.5 mm) and their separate average densities and the percentage of liver volume occupied by metastatic foci were calculated. The histograms represent the average values of the experiment. *Differences in average values of metastasis volume were statistically significant with respect to control mice ($P<0.01$) according by t'Student test. VLA-4 synthetic inhibitor was mixed with PAMAM-G3.5 macromolecule in a 1:4 ratio (CPN/PAMAM-G3.5). First, mice were given one intraperitoneal injection of either PAMAM-G3.5 or CPN/ PAMAM-G3.5 (2.5 mg/kg) 1 hour prior cancer cell inoculation and then, the same dose was repeated on days 2,3,8,9,10 and 11 postinjection. As shown in FIG. 10, the hepatic volume fraction occupied by metastatic tissue decreased by 50% in treated Mouse groups as compared to vehicle-treated mice. Next, the microvessel density per surface unit of metastatic tissue was determined by morphometrical study of densitometrically discriminated CD31-expressing and ASMA-expressing microvessels. Both parameters were separately analyzed in metastases with different size from PAMA-G3.5- and CPN/PAMA-G3.5-treated mice. The histograms represented in FIG. 11 show that VLA-4 Inhibitor CPN/PAMAM-G3.5 treatment inhibits endothelial cell and myofibroblast recruitment into Co26 colon carcinoma hepatic metastases. On the other hand, the immunohistochemical characterization of hepatic-infiltrating inflammatory cells demonstrates that VLA-4 inhibitor treatment reduces leucocyte recruitment into unaffected hepatic tissue and not into metastatic tissue. Leucocyte recruitment was determined by the morphometrical assessment of CD45-expressing cell number in liver sections. Finally, the effect of synthetic VLA-4 inhibitor CPN/PAMAM-G3.5 was studied in an endothelial cell migration assay induced by tumor-derived soluble factors. HSE cells were placed in the upper compartment of a modified Boyden chamber and incubated with basal medium or Co26-CC-CM in the presence or absence of 25 μg/ml CPN/PAMAM-G3.5. The lower compartment contained basal medium. After 48 hours, migrated cells were analyzed. Differences in the number of migrated cells with respect to untreated HSE cells (*) or Co26-CC-CM-treated HSE cells (**) were statistically significant (P<0.01), by ANOVA and Bonferroni s post-hoc test. As shown in FIG. 13, the conditioned media from Co26 colon carcinoma cells (Co26-CC-CM) induced HSE migration through collagen type 1. This effect was completely neutralized by the addition of CPN/PAMAM-G3.5.

In summary, we have described a new family of inhibitors of the VLA-4NCAM-1 interaction that 1) block the in vitro adhesion of melanoma cells to microvascular endothelium induced by proinflammatory cytokines and oxidative stress, 2) prevent melanoma cell production of VEGF induced by VCAM-1 in vitro, 3) inhibit in vitro human lymphocyte and leukemia cell attachment to VCAM-1 substrate and in vivo leucocyte recruitment into unaffected tissue of liver bearing colon carcinoma metastases. 4) inhibit hepatic colon carcinoma metastasis. 5) Inhibit endothelial cell and myofibroblast recruitment into colon carcinoma hepatic metastases in vivo and endothelial cell migration induced by tumor-derived soluble factors in vitro, which correlate with decreased angiogenesis and low metastatic growth in vivo and 6) exhibit in general a potent antimetastatic, anti-inflammatory and anti-angiogenic activity in vivo. These small synthetic molecules fulfill the bioavailability requirements proposed by Lipinski et al.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

The invention claimed is:
1. A compound of formula (I)

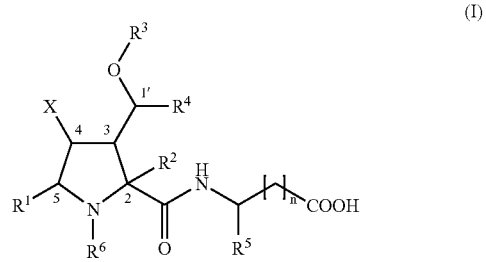

or a salt thereof, wherein:
n is selected from 0 to 5;
each of $R^1$, $R^3$ and $R^4$ is individually selected from a substituted or unsubstituted cyclic, linear or branched C1-C8 alkyl group and a substituted or unsubstituted phenyl, benzyl, aryl or heteroaryl group;
wherein each of $R^1$, $R^3$ and $R^4$ is optionally substituted with 1-6 atoms or groups selected from halogen; linear, branched or cyclic alkyl or alkoxy; benzyloxy; trifluoromethyl; trichloromethyl; nitro; hydroxyl and amino groups;
$R^2$ is selected from a hydrogen atom and a C1-C8 linear or branched alkyl group;
each of $R^5$ and $R^6$ is individually selected from a hydrogen atom; a straight, branched or cyclic alkyl, aryl, heteroaryl, mono- or polysubstituted aryl group; a mono- or polysubstituents heteroaryl group; a benzyl group; and a mono- or polysubstituted benzyl group; and
X is selected from a nitro group, an amido group and an amino group.

2. A compound according to claim 1, wherein X is a nitro group and each of $R^5$ and $R^6$ is a hydrogen atom.

3. A compound according to claim 2, wherein $R^1$ is selected from a substituted or unsubstituted cyclic, linear or branched C1-C8 alkyl and a phenyl group.

4. A compound according to claim 2, wherein $R^2$ is selected from a hydrogen atom and a methyl group.

5. A compound according to claim 2, wherein $R^3$ is a substituted or unsubstituted benzyl group.

6. A compound according to claim 2, wherein $R^4$ is a linear or branched C1-C8 alkyl group.

7. A compound according to claim 2, wherein:
$R^1$ is selected from a phenyl, cyclohexyl, cyclopropyl and substituted or unsubstituted butyl group;
$R^2$ is selected from a hydrogen atom and a methyl group;
$R^3$ is a substituted or unsubstituted benzyl group, wherein the substituents are one or two fluorine atoms;
$R^4$ is selected from an isopropyl group and a sec-butyl group;
and n is 0.

8. A method for the preparation of a pharmaceutical composition comprising combining at least one compound according to claim 1 with a pharmaceutically acceptable vehicle.

9. A pharmaceutical composition comprising at least one compound according to claim 1 with a pharmaceutically acceptable vehicle.

* * * * *